US010645908B2

(12) United States Patent
Seltzer et al.

(10) Patent No.: US 10,645,908 B2
(45) Date of Patent: May 12, 2020

(54) SYSTEMS AND METHODS FOR PROVIDING A SOUND MASKING ENVIRONMENT

(71) Applicant: Radio Systems Corporation, Knoxville, TN (US)

(72) Inventors: Richard Alan Seltzer, Knoxville, TN (US); Jon Huber, Knoxville, TN (US); Geoffrey Kyle Gift, Knoxville, TN (US)

(73) Assignee: RADIO SYSTEMS CORPORATION, Knoxville, TN (US)

( * ) Notice: Subject to any disclaimer, the term of this patent is extended or adjusted under 35 U.S.C. 154(b) by 0 days.

(21) Appl. No.: 16/266,781

(22) Filed: Feb. 4, 2019

(65) Prior Publication Data
US 2019/0166802 A1 Jun. 6, 2019

Related U.S. Application Data

(63) Continuation-in-part of application No. 15/078,499, filed on Mar. 23, 2016, now Pat. No. 10,231,440.
(Continued)

(51) Int. Cl.
*G08B 23/00* (2006.01)
*A01K 29/00* (2006.01)
(Continued)

(52) U.S. Cl.
CPC .......... *A01K 29/005* (2013.01); *A01K 27/001* (2013.01); *A61B 5/165* (2013.01);
(Continued)

(58) Field of Classification Search
CPC .... A01K 29/005; A01K 27/001; A61B 5/165; A61B 5/7282; G10K 11/175; G10K 11/178; G10L 21/0232; G10L 25/51
See application file for complete search history.

(56) References Cited

U.S. PATENT DOCUMENTS 2,741,224 A 4/1956 Putnam
3,182,211 A 5/1965 Maratuech et al.
(Continued)

FOREIGN PATENT DOCUMENTS

CN 101112181 A 1/2008
CN 101937015 A 1/2011
(Continued)

OTHER PUBLICATIONS

Eileen—How to Protect Your Dog From Loud and Scary Sounds (Year: 2013).*
(Continued)

*Primary Examiner* — Quang Pham
(74) *Attorney, Agent, or Firm* — Baker, Donelson, Bearman, Caldwell & Berkowitz PC

(57) ABSTRACT

A system is described herein that comprises a collar device including a sound masking component, the collar device including one or more collar device sensors for detecting physiological data of an animal. The system includes one or more environmental sensors configured to detect environmental data of the animal's environment and to transmit the environmental data to the collar device. The collar device comprises one or more applications running on at least one processor for detecting an occurrence of one or more events using at least one of the physiological data, the environmental data, and outcome data. The one or more applications are configured to use information of the one or more events to select a sound masking signal for delivery after the occurrence of the one or more events The system includes a sound masking component for delivering the sound masking signal.

32 Claims, 22 Drawing Sheets

Related U.S. Application Data which is a continuation-in-part of application No. 14/880,935, filed on Oct. 12, 2015, now abandoned, which is a continuation-in-part of application No. 14/741,159, filed on Jun. 16, 2015, now Pat. No. 10,045,512.

(60) Provisional application No. 62/625,477, filed on Feb. 2, 2018.

(51) Int. Cl.

| | | |
|---|---|---|
| *A01K 27/00* | (2006.01) | |
| *A61B 5/16* | (2006.01) | |
| *A61B 5/00* | (2006.01) | |
| *G10L 21/0232* | (2013.01) | |
| *G10K 11/175* | (2006.01) | |
| *G10L 25/51* | (2013.01) | |
| *G10K 11/178* | (2006.01) | |

(52) U.S. Cl.
CPC .......... *A61B 5/7282* (2013.01); *G10K 11/175* (2013.01); *G10L 21/0232* (2013.01); *G10K 11/178* (2013.01); *G10L 25/51* (2013.01)

(56) References Cited

U.S. PATENT DOCUMENTS

| | | |
|---|---|---|
| 3,184,730 A | 5/1965 | Irish |
| 3,500,373 A | 3/1970 | Arthur |
| 3,735,757 A | 5/1973 | MacFarland |
| 4,426,884 A | 1/1984 | Polchaninoff |
| 4,783,646 A | 11/1988 | Matsuzaki |
| 4,794,402 A | 12/1988 | Gonda et al. |
| 4,802,482 A | 2/1989 | Gonda et al. |
| 4,947,795 A | 8/1990 | Farkas |
| 4,969,418 A | 11/1990 | Jones |
| 5,054,428 A | 10/1991 | Farkus |
| 5,159,580 A | 10/1992 | Andersen et al. |
| 5,161,485 A | 11/1992 | McDade |
| 5,182,032 A | 1/1993 | Dickie et al. |
| 5,207,178 A | 5/1993 | McDade et al. |
| 5,207,179 A | 5/1993 | Arthur et al. |
| 5,526,006 A | 6/1996 | Akahane et al. |
| 5,559,498 A | 9/1996 | Westrick et al. |
| 5,576,972 A | 11/1996 | Harrison |
| 5,586,521 A | 12/1996 | Kelley |
| 5,601,054 A | 2/1997 | So |
| 5,642,690 A | 7/1997 | Calabrese et al. |
| 5,794,569 A | 8/1998 | Titus et al. |
| 5,815,077 A | 9/1998 | Christiansen |
| 5,844,489 A | 12/1998 | Yarnall, Jr. et al. |
| 5,857,433 A | 1/1999 | Files |
| 5,870,029 A | 2/1999 | Otto et al. |
| 5,872,516 A | 2/1999 | Bonge, Jr. |
| 5,886,669 A | 3/1999 | Kita |
| 5,923,254 A | 7/1999 | Brune |
| 5,927,233 A | 7/1999 | Mainini et al. |
| 5,933,079 A | 8/1999 | Frink |
| 5,934,225 A | 8/1999 | Williams |
| 5,949,350 A | 9/1999 | Girard et al. |
| 5,957,983 A | 9/1999 | Tominaga |
| 5,982,291 A | 11/1999 | Williams et al. |
| 6,016,100 A | 1/2000 | Boyd et al. |
| 6,019,066 A | 2/2000 | Taylor |
| 6,028,531 A | 2/2000 | Wanderlich |
| 6,047,664 A | 4/2000 | Lyerly |
| 6,067,018 A | 5/2000 | Skelton et al. |
| 6,075,443 A | 6/2000 | Schepps et al. |
| 6,166,643 A | 12/2000 | Janning et al. |
| 6,170,439 B1 | 1/2001 | Duncan et al. |
| 6,184,790 B1 | 2/2001 | Gerig |
| 6,196,990 B1 | 3/2001 | Zicherman |
| 6,204,762 B1 | 3/2001 | Dering et al. |
| 6,215,314 B1 | 4/2001 | Frankewich, Jr. |
| 6,230,031 B1 | 5/2001 | Barber |
| 6,230,661 B1 | 5/2001 | Yarnall, Jr. et al. |
| 6,232,880 B1 | 5/2001 | Anderson et al. |
| 6,271,757 B1 | 8/2001 | Touchton et al. |
| 6,327,999 B1 | 12/2001 | Gerig |
| 6,353,390 B1 | 3/2002 | Beri et al. |
| 6,360,697 B1 | 3/2002 | Williams |
| 6,360,698 B1 | 3/2002 | Stapelfeld et al. |
| 6,404,338 B1 | 6/2002 | Koslar |
| 6,415,742 B1 | 7/2002 | Lee et al. |
| 6,426,464 B1 | 7/2002 | Spellman et al. |
| 6,427,079 B1 | 7/2002 | Schneider et al. |
| 6,431,121 B1 | 8/2002 | Mainini et al. |
| 6,431,122 B1 | 8/2002 | Westrick et al. |
| 6,441,778 B1 | 8/2002 | Durst et al. |
| 6,459,378 B2 | 10/2002 | Gerig |
| 6,487,992 B1 | 12/2002 | Hollis |
| 6,561,137 B2 | 5/2003 | Oakman |
| 6,581,546 B1 | 6/2003 | Dalland et al. |
| 6,588,376 B1 | 7/2003 | Groh |
| 6,598,563 B2 | 7/2003 | Kim et al. |
| 6,600,422 B2 | 7/2003 | Barry et al. |
| 6,637,376 B2 | 10/2003 | Lee et al. |
| 6,657,544 B2 | 12/2003 | Barry et al. |
| 6,668,760 B2 | 12/2003 | Groh et al. |
| 6,700,492 B2 | 3/2004 | Touchton et al. |
| 6,747,555 B2 | 6/2004 | Fellenstein et al. |
| 6,798,887 B1 * | 9/2004 | Andre .............. G06F 21/83 381/1 |
| 6,799,537 B1 | 10/2004 | Liao |
| 6,807,720 B2 | 10/2004 | Brune et al. |
| 6,820,025 B2 | 11/2004 | Bachmann et al. |
| 6,825,768 B2 | 11/2004 | Stapelfeld et al. |
| 6,830,012 B1 | 12/2004 | Swan |
| 6,833,790 B2 | 12/2004 | Mejia et al. |
| 6,874,447 B1 | 4/2005 | Kobett |
| 6,888,502 B2 | 5/2005 | Beigel et al. |
| 6,901,883 B2 | 6/2005 | Gillis et al. |
| 6,903,682 B1 | 6/2005 | Maddox |
| 6,907,844 B1 | 6/2005 | Crist et al. |
| 6,907,883 B2 | 6/2005 | Lin |
| 6,921,089 B2 | 7/2005 | Groh et al. |
| 6,923,146 B2 | 8/2005 | Korbitz et al. |
| 6,928,958 B2 | 8/2005 | Crist et al. |
| 6,937,647 B1 | 8/2005 | Boyd et al. |
| 6,956,483 B2 | 10/2005 | Schmitt et al. |
| 6,970,090 B1 | 11/2005 | Sciarra |
| 7,061,385 B2 | 6/2006 | Fong et al. |
| 7,079,024 B2 | 7/2006 | Alarcon et al. |
| 7,114,466 B1 | 10/2006 | Mayer |
| 7,142,167 B2 | 11/2006 | Rochelle et al. |
| 7,164,354 B1 | 1/2007 | Panzer |
| 7,173,535 B2 | 2/2007 | Bach et al. |
| 7,198,009 B2 | 4/2007 | Crist et al. |
| 7,222,589 B2 | 5/2007 | Lee et al. |
| 7,249,572 B2 | 7/2007 | Goetzl et al. |
| 7,252,051 B2 | 8/2007 | Napolez et al. |
| 7,259,718 B2 | 8/2007 | Patterson et al. |
| 7,267,081 B2 | 9/2007 | Steinbacher |
| 7,275,502 B2 | 10/2007 | Boyd et al. |
| 7,296,540 B2 | 11/2007 | Boyd |
| 7,319,397 B2 | 1/2008 | Chung et al. |
| 7,328,671 B2 | 2/2008 | Kates |
| 7,339,474 B2 | 3/2008 | Easley et al. |
| 7,382,328 B2 | 6/2008 | Lee et al. |
| 7,394,390 B2 | 7/2008 | Gerig |
| 7,395,966 B2 | 7/2008 | Braiman |
| 7,404,379 B2 | 7/2008 | Nottingham et al. |
| 7,411,492 B2 | 8/2008 | Greenberg et al. |
| 7,426,906 B2 | 9/2008 | Nottingham et al. |
| 7,434,541 B2 | 10/2008 | Kates |
| 7,443,298 B2 | 10/2008 | Cole et al. |
| 7,477,155 B2 | 1/2009 | Bach et al. |
| 7,503,285 B2 | 3/2009 | Mainini et al. |
| 7,518,275 B2 | 4/2009 | Suzuki et al. |
| 7,518,522 B2 | 4/2009 | So et al. |
| 7,538,679 B2 | 5/2009 | Shanks |
| 7,546,817 B2 | 6/2009 | Moore |
| 7,552,699 B2 | 6/2009 | Moore |

(56) References Cited

U.S. PATENT DOCUMENTS

| | | |
|---|---|---|
| 7,562,640 B2 | 7/2009 | Lalor |
| 7,565,885 B2 | 7/2009 | Moore |
| 7,574,979 B2 | 8/2009 | Nottingham et al. |
| 7,583,931 B2 | 9/2009 | Eu et al. |
| 7,602,302 B2 | 10/2009 | Hokuf et al. |
| 7,612,668 B2 | 11/2009 | Harvey |
| 7,616,124 B2 | 11/2009 | Paessel et al. |
| 7,656,291 B2 | 2/2010 | Rochelle et al. |
| 7,667,599 B2 | 2/2010 | Mainini et al. |
| 7,667,607 B2 | 2/2010 | Gerig et al. |
| 7,680,645 B2 | 3/2010 | Li et al. |
| 7,705,736 B1 | 4/2010 | Kedziora |
| 7,710,263 B2 | 5/2010 | Boyd |
| 7,760,137 B2 | 7/2010 | Martucci et al. |
| 7,779,788 B2 | 8/2010 | Moore |
| 7,786,876 B2 | 8/2010 | Troxler et al. |
| 7,804,724 B2 | 9/2010 | Way |
| 7,814,865 B2 | 10/2010 | Tracy et al. |
| 7,828,221 B2 | 11/2010 | Kwon, II |
| 7,830,257 B2 | 11/2010 | Hassell |
| 7,834,769 B2 | 11/2010 | Hinkle et al. |
| 7,841,301 B2 | 11/2010 | Mainini et al. |
| 7,856,947 B2 | 12/2010 | Giunta |
| 7,864,057 B2 | 1/2011 | Milnes et al. |
| 7,868,912 B2 | 1/2011 | Venetianer et al. |
| 7,900,585 B2 | 3/2011 | Lee et al. |
| 7,918,190 B2 | 4/2011 | Belcher et al. |
| 7,944,359 B2 | 5/2011 | Fong et al. |
| 7,946,252 B2 | 5/2011 | Lee, IV et al. |
| 7,978,078 B2 | 7/2011 | Copeland et al. |
| 7,996,983 B2 | 8/2011 | Lee et al. |
| 8,011,327 B2 | 9/2011 | Mainini et al. |
| 8,047,161 B2 | 11/2011 | Moore et al. |
| 8,049,630 B2 | 11/2011 | Chao Cheng et al. |
| 8,065,978 B2 | 11/2011 | Duncan et al. |
| 8,069,823 B2 | 12/2011 | Mainini et al. |
| 8,098,164 B2 | 1/2012 | Gerig et al. |
| 8,159,355 B2 | 4/2012 | Gerig et al. |
| 8,185,345 B2 | 5/2012 | Mainini |
| 8,232,909 B2 | 7/2012 | Kroeger et al. |
| 8,240,085 B2 | 8/2012 | Hill |
| 8,269,504 B2 | 9/2012 | Gerig |
| 8,274,396 B2 | 9/2012 | Gurley et al. |
| 8,297,233 B2 | 10/2012 | Rich et al. |
| 8,342,134 B2 | 1/2013 | Lee et al. |
| 8,342,135 B2 | 1/2013 | Peinetti et al. |
| 8,430,064 B2 | 4/2013 | Groh et al. |
| 8,436,735 B2 | 5/2013 | Mainini et al. |
| 8,447,510 B2 | 5/2013 | Fitzpatrick et al. |
| 8,451,130 B2 | 5/2013 | Mainini |
| 8,456,296 B2 | 6/2013 | Piltonen et al. |
| 8,483,262 B2 | 7/2013 | Mainini et al. |
| 8,714,113 B2 | 5/2014 | Lee, IV et al. |
| 8,715,824 B2 | 5/2014 | Rawlings et al. |
| 8,736,499 B2 | 5/2014 | Goetzl et al. |
| 8,779,925 B2 | 7/2014 | Rich et al. |
| 8,803,692 B2 | 8/2014 | Goetzl et al. |
| 8,807,089 B2 | 8/2014 | Brown et al. |
| 8,823,513 B2 | 9/2014 | Jameson et al. |
| 8,854,215 B1 | 10/2014 | Ellis et al. |
| 8,866,605 B2 | 10/2014 | Gibson |
| 8,908,034 B2 | 12/2014 | Bordonaro |
| 8,917,172 B2 | 12/2014 | Charych |
| 8,947,240 B2 | 2/2015 | Mainini |
| 8,967,085 B2 | 3/2015 | Gillis et al. |
| 9,035,773 B2 | 5/2015 | Petersen et al. |
| 9,125,380 B2 | 9/2015 | Deutsch |
| 9,131,660 B2 | 9/2015 | Womble |
| 9,186,091 B2 | 11/2015 | Mainini et al. |
| 9,204,251 B1 | 12/2015 | Mendelson et al. |
| 9,307,745 B2 | 4/2016 | Mainini |
| 9,861,076 B2 | 1/2018 | Rochelle et al. |
| 2002/0010390 A1 | 1/2002 | Guice et al. |
| 2002/0015094 A1 | 2/2002 | Kuwano et al. |
| 2002/0036569 A1 | 3/2002 | Martin |
| 2002/0092481 A1 | 7/2002 | Spooner |
| 2002/0103610 A1 | 8/2002 | Bachmann et al. |
| 2002/0196151 A1 | 12/2002 | Troxler |
| 2003/0034887 A1 | 2/2003 | Crabtree et al. |
| 2003/0035051 A1 | 2/2003 | Cho et al. |
| 2003/0116099 A1 | 6/2003 | Kim et al. |
| 2003/0169207 A1 | 9/2003 | Beigel et al. |
| 2003/0179140 A1 | 9/2003 | Patterson et al. |
| 2003/0218539 A1 | 11/2003 | Hight |
| 2004/0108939 A1 | 6/2004 | Giunta |
| 2004/0162875 A1 | 8/2004 | Brown |
| 2005/0000469 A1 | 1/2005 | Giunta et al. |
| 2005/0007251 A1 | 1/2005 | Crabtree et al. |
| 2005/0020279 A1 | 1/2005 | Markhovsky et al. |
| 2005/0035865 A1 | 2/2005 | Brennan et al. |
| 2005/0059909 A1 | 3/2005 | Burgess |
| 2005/0066912 A1 | 3/2005 | Korbitz et al. |
| 2005/0081797 A1 | 4/2005 | Laitinen et al. |
| 2005/0139169 A1 | 6/2005 | So et al. |
| 2005/0145196 A1 | 7/2005 | Crist et al. |
| 2005/0145198 A1 | 7/2005 | Crist et al. |
| 2005/0145200 A1 | 7/2005 | Napolez et al. |
| 2005/0172912 A1 | 8/2005 | Crist et al. |
| 2005/0217606 A1 | 10/2005 | Lee et al. |
| 2005/0231353 A1 | 10/2005 | DiPoala et al. |
| 2005/0235924 A1 | 10/2005 | Lee et al. |
| 2005/0258715 A1 | 11/2005 | Schlabach et al. |
| 2005/0263106 A1 | 12/2005 | Steinbacher |
| 2005/0280546 A1 | 12/2005 | Ganley et al. |
| 2005/0288007 A1 | 12/2005 | Benco et al. |
| 2006/0000015 A1 | 1/2006 | Duncan |
| 2006/0011145 A1 | 1/2006 | Kates et al. |
| 2006/0027185 A1 | 2/2006 | Troxler et al. |
| 2006/0092676 A1 | 5/2006 | Liptak et al. |
| 2006/0102101 A1 | 5/2006 | Kim |
| 2006/0112901 A1 | 6/2006 | Gomez |
| 2006/0191491 A1 | 8/2006 | Nottingham et al. |
| 2006/0196445 A1 | 9/2006 | Kates |
| 2006/0197672 A1 | 9/2006 | Talamas, Jr. et al. |
| 2006/0202818 A1 | 9/2006 | Greenberg et al. |
| 2007/0011339 A1 | 1/2007 | Brown |
| 2007/0103296 A1* | 5/2007 | Paessel ............ A01K 11/006 340/539.22 |
| 2007/0197878 A1* | 8/2007 | Shklarski ............ A61B 5/02055 600/300 |
| 2007/0204803 A1 | 9/2007 | Ramsay |
| 2007/0204804 A1 | 9/2007 | Swanson et al. |
| 2007/0249470 A1 | 10/2007 | Niva et al. |
| 2007/0266959 A1 | 11/2007 | Brooks et al. |
| 2008/0004539 A1 | 1/2008 | Ross |
| 2008/0017133 A1 | 1/2008 | Moore |
| 2008/0036610 A1 | 2/2008 | Hokuf et al. |
| 2008/0055154 A1 | 3/2008 | Martucci et al. |
| 2008/0055155 A1 | 3/2008 | Hensley et al. |
| 2008/0058670 A1 | 3/2008 | Mainini et al. |
| 2008/0061978 A1 | 3/2008 | Huang |
| 2008/0061990 A1 | 3/2008 | Milnes et al. |
| 2008/0119757 A1 | 5/2008 | Winter |
| 2008/0129457 A1 | 6/2008 | Ritter et al. |
| 2008/0141949 A1 | 6/2008 | Taylor |
| 2008/0143516 A1 | 6/2008 | Mock et al. |
| 2008/0156277 A1 | 7/2008 | Mainini et al. |
| 2008/0163827 A1 | 7/2008 | Goetzl |
| 2008/0163829 A1 | 7/2008 | Lee et al. |
| 2008/0168949 A1 | 7/2008 | Belcher et al. |
| 2008/0168950 A1 | 7/2008 | Moore et al. |
| 2008/0186167 A1 | 8/2008 | Ramachandra |
| 2008/0186197 A1 | 8/2008 | Rochelle et al. |
| 2008/0204322 A1 | 8/2008 | Oswald et al. |
| 2008/0236514 A1 | 10/2008 | Johnson et al. |
| 2008/0252527 A1 | 10/2008 | Garcia |
| 2008/0272908 A1 | 11/2008 | Boyd |
| 2009/0000566 A1 | 1/2009 | Kim |
| 2009/0002188 A1 | 1/2009 | Greenberg |
| 2009/0012355 A1 | 1/2009 | Lin |
| 2009/0020002 A1 | 1/2009 | Williams et al. |
| 2009/0025651 A1 | 1/2009 | Lalor |
| 2009/0031966 A1 | 2/2009 | Kates |

(56) References Cited

U.S. PATENT DOCUMENTS

| | | | |
|---|---|---|---|
| 2009/0061772 A1* | 3/2009 | Moon | G01N 27/4045 |
| | | | 455/41.2 |
| 2009/0082830 A1 | 3/2009 | Folkerts et al. | |
| 2009/0102668 A1 | 4/2009 | Thompson et al. | |
| 2009/0224909 A1 | 9/2009 | Derrick et al. | |
| 2009/0239586 A1 | 9/2009 | Boeve et al. | |
| 2009/0289785 A1 | 11/2009 | Leonard | |
| 2009/0289844 A1 | 11/2009 | Palsgrove et al. | |
| 2010/0008011 A1 | 1/2010 | Ogram | |
| 2010/0033339 A1 | 2/2010 | Gurley et al. | |
| 2010/0047119 A1 | 2/2010 | Cressy | |
| 2010/0049364 A1 | 2/2010 | Landry et al. | |
| 2010/0107985 A1 | 5/2010 | O'Hare | |
| 2010/0139576 A1 | 6/2010 | Kim et al. | |
| 2010/0154721 A1 | 6/2010 | Gerig et al. | |
| 2010/0231391 A1 | 9/2010 | Dror et al. | |
| 2010/0238022 A1 | 9/2010 | Au et al. | |
| 2010/0315241 A1 | 12/2010 | Jow | |
| 2011/0140967 A1 | 6/2011 | Lopez Pou et al. | |
| 2012/0000431 A1 | 1/2012 | Khoshkish et al. | |
| 2012/0006282 A1 | 1/2012 | Kates | |
| 2012/0037088 A1 | 2/2012 | Altenhofen | |
| 2012/0078139 A1 | 3/2012 | Aldridge et al. | |
| 2012/0132151 A1 | 5/2012 | Touchton et al. | |
| 2012/0165012 A1 | 6/2012 | Fischer et al. | |
| 2012/0188370 A1 | 7/2012 | Bordonaro | |
| 2012/0236688 A1 | 9/2012 | Spencer et al. | |
| 2012/0312250 A1 | 12/2012 | Jesurum | |
| 2013/0099920 A1 | 4/2013 | Song et al. | |
| 2013/0099922 A1 | 4/2013 | Lohbihler | |
| 2013/0141237 A1 | 6/2013 | Goetzl et al. | |
| 2013/0157564 A1 | 6/2013 | Curtis et al. | |
| 2013/0169441 A1 | 7/2013 | Wilson | |
| 2013/0298846 A1* | 11/2013 | Mainini | A01K 15/02 |
| | | | 119/719 |
| 2013/0321159 A1 | 12/2013 | Schofield et al. | |
| 2014/0020635 A1 | 1/2014 | Sayers et al. | |
| 2014/0053788 A1 | 2/2014 | Riddell | |
| 2014/0062695 A1 | 3/2014 | Rosen et al. | |
| 2014/0069350 A1 | 3/2014 | Riddell | |
| 2014/0073939 A1 | 3/2014 | Rodriguez-Llorente et al. | |
| 2014/0120943 A1 | 5/2014 | Shima | |
| 2014/0123912 A1* | 5/2014 | Menkes | A61B 5/1105 |
| | | | 119/859 |
| 2014/0132608 A1 | 5/2014 | Mund et al. | |
| 2014/0174376 A1 | 6/2014 | Touchton et al. | |
| 2014/0228649 A1* | 8/2014 | Rayner | A61B 5/1118 |
| | | | 600/301 |
| 2014/0253389 A1 | 9/2014 | Beauregard | |
| 2014/0261235 A1 | 9/2014 | Rich et al. | |
| 2014/0267299 A1* | 9/2014 | Couse | G06T 11/206 |
| | | | 345/440.2 |
| 2014/0275824 A1 | 9/2014 | Couse et al. | |
| 2014/0276278 A1* | 9/2014 | Smith | A63B 71/1291 |
| | | | 601/133 |
| 2014/0307888 A1* | 10/2014 | Alderson | H04R 3/002 |
| | | | 381/71.8 |
| 2014/0320347 A1 | 10/2014 | Rochelle et al. | |
| 2014/0343599 A1* | 11/2014 | Smith | A61B 17/1327 |
| | | | 606/202 |
| 2015/0040840 A1 | 2/2015 | Muetzel et al. | |
| 2015/0043744 A1* | 2/2015 | Lagodzinski | H04R 3/12 |
| | | | 381/73.1 |
| 2015/0053144 A1 | 2/2015 | Bianchi et al. | |
| 2015/0075446 A1 | 3/2015 | Hu | |
| 2015/0080013 A1 | 3/2015 | Venkatraman et al. | |
| 2015/0107531 A1 | 4/2015 | Golden | |
| 2015/0149111 A1 | 5/2015 | Kelly et al. | |
| 2015/0163412 A1 | 6/2015 | Holley et al. | |
| 2015/0172872 A1 | 6/2015 | Alsehly et al. | |
| 2015/0173327 A1 | 6/2015 | Gerig et al. | |
| 2015/0199490 A1 | 7/2015 | Iancu et al. | |
| 2015/0223013 A1 | 8/2015 | Park et al. | |
| 2015/0289111 A1 | 10/2015 | Ozkan et al. | |
| 2015/0350848 A1* | 12/2015 | Eramian | H04W 4/90 |
| | | | 455/404.2 |
| 2015/0358768 A1* | 12/2015 | Luna | G01S 11/06 |
| | | | 455/456.1 |
| 2016/0015005 A1 | 1/2016 | Brown, Jr. et al. | |
| 2016/0021506 A1* | 1/2016 | Bonge, Jr. | A01K 27/009 |
| | | | 717/173 |
| 2016/0021850 A1 | 1/2016 | Stapelfeld et al. | |
| 2016/0044444 A1 | 2/2016 | Rattner et al. | |
| 2016/0084801 A1* | 3/2016 | Robinson | G01N 29/11 |
| | | | 73/599 |
| 2016/0094419 A1 | 3/2016 | Peacock et al. | |
| 2016/0102879 A1 | 4/2016 | Guest et al. | |
| 2016/0150362 A1 | 5/2016 | Shaprio et al. | |
| 2016/0174099 A1* | 6/2016 | Goldfain | G06F 1/1684 |
| | | | 375/130 |
| 2016/0178392 A1* | 6/2016 | Goldfain | G16H 40/63 |
| | | | 702/104 |
| 2016/0187454 A1* | 6/2016 | Orman | G01S 3/8022 |
| | | | 367/124 |
| 2016/0253987 A1* | 9/2016 | Chattell | G10K 11/175 |
| | | | 381/73.1 |
| 2016/0335917 A1* | 11/2016 | Lydecker | G09B 21/008 |
| 2016/0363664 A1 | 12/2016 | Mindell et al. | |
| 2017/0323630 A1* | 11/2017 | Stickney | G10K 11/178 |
| 2018/0027772 A1 | 2/2018 | Gordon et al. | |
| 2018/0077509 A1* | 3/2018 | Jones | H04R 1/406 |
| 2018/0078735 A1* | 3/2018 | Dalgleish | A61B 5/6898 |
| 2018/0094451 A1 | 4/2018 | Peter et al. | |
| 2018/0188351 A1* | 7/2018 | Jones | G06Q 10/08 |
| 2018/0210704 A1* | 7/2018 | Jones | B62B 3/00 |
| 2018/0234134 A1 | 8/2018 | Tang et al. | |
| 2018/0235182 A1* | 8/2018 | Bocknek | A01K 29/005 |
| 2018/0315262 A1 | 11/2018 | Love et al. | |
| 2019/0013003 A1* | 1/2019 | Baughman | G06F 3/167 |
| 2019/0165832 A1* | 5/2019 | Khanduri | H04B 3/237 |

FOREIGN PATENT DOCUMENTS

| | | |
|---|---|---|
| CN | 101112181 B | 11/2012 |
| CN | 102793568 B | 12/2014 |
| JP | H0974774 A | 3/1997 |
| KR | 20130128704 A | 11/2013 |
| WO | WO-02060240 A3 | 2/2003 |
| WO | WO-2006000015 A1 | 1/2006 |
| WO | WO-2008085812 A2 | 7/2008 |
| WO | WO-2008140992 A1 | 11/2008 |
| WO | WO-2009105243 A2 | 8/2009 |
| WO | WO-2009106896 A2 | 9/2009 |
| WO | WO-2011055004 A1 | 5/2011 |
| WO | WO-2011136816 A1 | 11/2011 |
| WO | WO-2012122607 A1 | 9/2012 |
| WO | WO-2015015047 A1 | 2/2015 |
| WO | WO-2016204799 A1 | 12/2016 |

OTHER PUBLICATIONS

Extended European Search Report for Application No. EP17180645, dated May 9, 2018, 7 pages.
Baba A.I., et al., "Calibrating Time of Flight in Two Way Ranging," IEEE Xplore Digital Library, Dec. 2011, pp. 393-397.
Extended European Search Report for European Application No. 11784149.4 dated Nov. 17, 2017, 7 pages.
Extended European Search Report for European Application No. 15735439.0 dated Oct. 18, 2017, 9 pages.
Extended European Search Report for European Application No. 15895839.7 dated Oct. 9, 2018, 5 pages.
Extended European Search Report for European Application No. 17162289.7 dated Aug. 31, 2017, 7 pages.
High Tech Products, Inc: "Human Contain Model X-10 Rechargeable Muti-function Electronic Dog Fence Ultra-system", Internet citation, Retrieved from the Internet: URL:http://web.archive.org/web/20120112221915/http://hightechpet.com/user_Manuals/HC%20X-10_Press.pdf retrieved on Apr. 10, 2017], Apr. 28, 2012, pp. 1-32, XP008184171.

(56) References Cited

OTHER PUBLICATIONS

International Preliminary Report for Patentability Chapter II for International Application No. PCT/US2014/024875 dated Mar. 12, 2015, 17 pages.
International Preliminary Report on Patentability for Application No. PCT/US2015/043653 dated Dec. 19, 2017, 14 pages.
International Search Report and Written Opinion for Application No. PCT/US2018/013737 dated Mar. 7, 2018, 8 pages.
International Search Report and Written Opinion for Application No. PCT/US2018/013738 dated Mar. 20, 2018, 6 pages.
International Search Report and Written Opinion for Application No. PCT/US2018/013740 dated Mar. 20, 2018, 6 pages.
International Search Report and Written Opinion for Application No. PCT/US2018/019887 dated May 8, 2018, 10 pages.
International Search Report and Written Opinion for International Application No. PCT/US2014/024875 dated Jun. 27, 2014, 12 pages.
International Search Report for International Application No. PCT/US2014/020344 dated Jun. 5, 2014, 2 pages.
International Search Report for International Application No. PCT/US2014/066650 dated Feb. 19, 2015, 3 pages (Outgoing).
International Search Report for International Application No. PCT/US2015/010864, Form PCT/ISA/210 dated Apr. 13, 2015, 2 pages.
International Search Report for International Application No. PCT/US2015/043653, Form PCT/ISA/210 dated Oct. 23, 2015, 2 pages.
Notification of Transmittal of the International Search Report and the Written Opinion of the International Searching Authority for International Application No. PCT/US2015/043653, Form PCT/ISA/220 dated Oct. 23, 2015, 1 page.
Notification of Transmittal of the International Search Report and Written Opinion for the International Application No. PCT/US2014/066650 dated Feb. 19, 2015, 1 page.
Welch et al., "An Introduction to the Kalman Filter," Department of Computer Science, Jul. 24, 2006, pp. 1-16.
Written Opinion for International Application No. PCT/US2014/066650 dated Feb. 19, 2015, 15 pages(outgoing).
Written Opinion for International Application No. PCT/US2015/043653, Form PCT/ISA/237 dated Oct. 23, 2015, 13 pages.
Written Opinion of the International Application No. PCT/US2015/010864, Form PCT/ISA/237 dated Apr. 13, 2015, 6 pages.

* cited by examiner

SYSTEMS AND METHODS FOR PROVIDING A SOUND MASKING ENVIRONMENT

CROSS REFERENCE TO RELATED APPLICATIONS

This application is a continuation in part application of U.S. application Ser. No. 15/078,499, filed Mar. 23, 2016, which is a continuation in part application of U.S. patent application Ser. No. 14/880,935, filed Oct. 12, 2015, which is a continuation in part application of U.S. patent application Ser. No. 14/741,159, filed Jun. 16, 2015. This application claims the benefit of U.S. Patent Application No. 62/625,477, filed Feb. 2, 2018.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

As a result of work, school, and other obligations, most pet owners cannot be with their pet at every moment of every day. However, some pets, due to various conditions, behaviors, and circumstances, require some form of monitoring throughout each day or at least at particular times. This is particularly true if an owner allows a pet to freely roam a home premises in the owner's absence.

At times a dog's environment may present auditory disturbances. Dogs can hear noises at a much higher frequency than humans. While humans struggle to hear anything above 30,000 Hertz, dogs can hear noises well over 40,000 Hertz. Interestingly, there is little difference between humans and dogs at the lower end of the frequency scale. Dogs have as many as 18 muscles in their ears, enabling them to direct their ears towards the sound. Such ability to detect a wider array of audible signals may induce noise phobia in dogs. There is therefore a need in the art for improved wearable sound masking systems for dogs.

BRIEF DESCRIPTION OF THE DRAWINGS

So that the manner in which the present application can be better understood, certain illustrations and figures are appended hereto. It is to be noted, however, that the drawings illustrate only selected embodiments and elements of the systems and methods described herein and are therefore not to be considered limiting in scope for the systems and methods as described herein may admit to other equally effective embodiments and applications.

DETAILED DESCRIPTION

Figure 1:
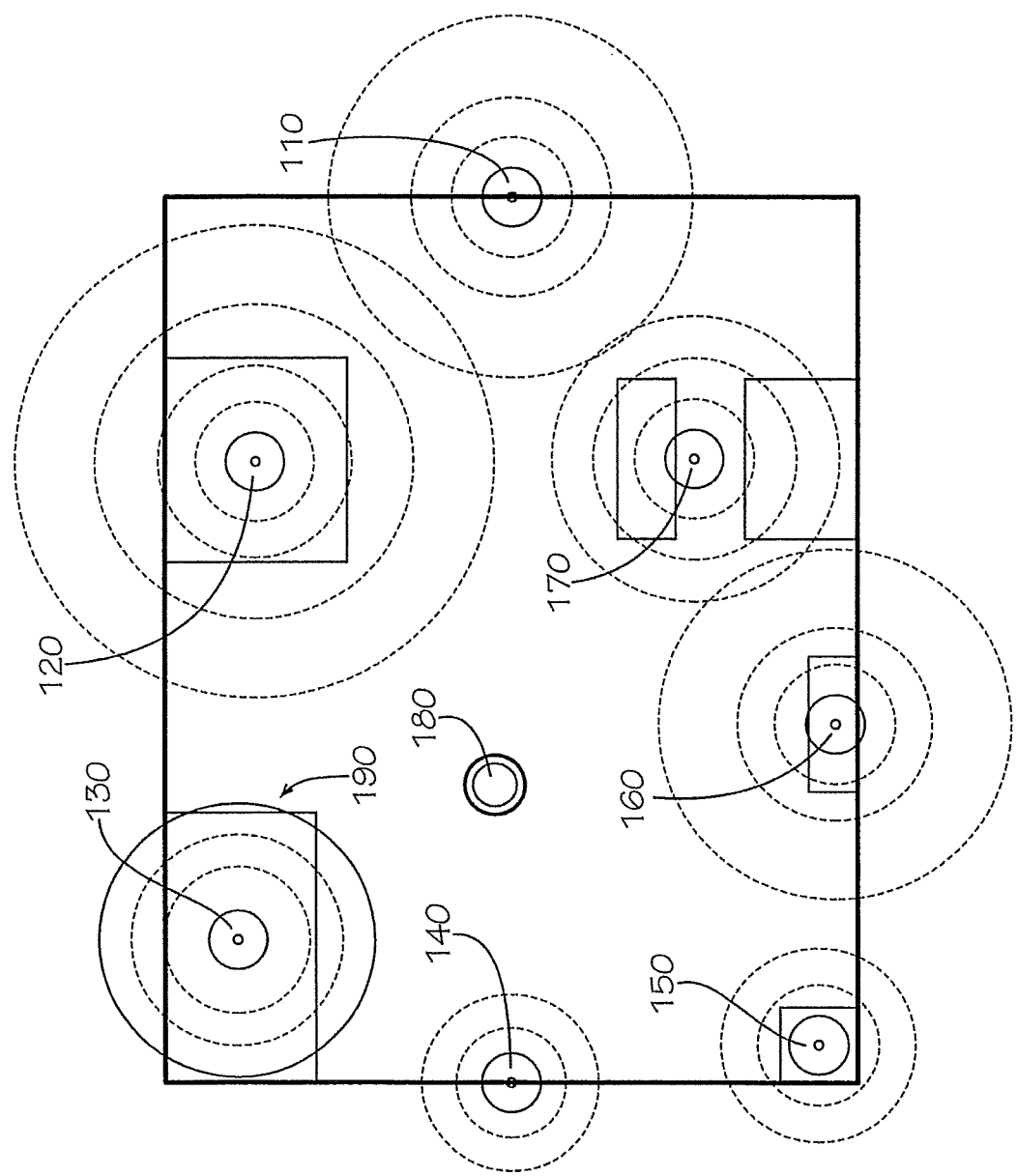
FIG. 1 shows beacons deployed at various locations in a home premises, under an embodiment.

The demographics of pet ownership have been changing. The size of pet dogs has been getting smaller, they stay inside the home longer per day; if not all day. Both young and older individuals are gravitating towards smaller dwellings. Metropolitan living is becoming more popular. As a result, apartments and condominiums in cities and municipalities are easing their restrictions related to dog occupancy in these smaller living spaces. Therefore, a market is being defined based on the needs for these (but not limited) to metropolitan pet owners.

Specifically looking at the needs of this demographic group, some of the more "rural" pet solutions do not apply. Coupled with the new technology platforms available and the prevalence of smart phones and internet availability, new solutions emerge. And in response to the general cry of consumers for products with more features and benefits with less complexity and "hassle", the systems and methods described herein answer that call.

Consider the reduced size of the pet's home in the metropolitan environment. The pet owners would like control of the pet's allowable whereabouts (stay out of the kitchen, ok in living room etc.), and knowledge of its routine activities (when did she sleep and where?, did she bark?, did she eat, drink and when? etc.). This disclosure provides for the simple set up of a monitoring/tracking/detection/training/avoidance system, easy configuration of system components, and optionally worldwide, real-time access to the information.

The systems and methods described herein include distributing pet beacons in a house at strategic locations to provide monitoring/tracking/detecting/training/avoidance functionality for pets. These devices are designed to periodically transmit a unique identification code along with functional parameters. Currently, such devices transmit signals for a distance of up to 70 meters. They are designed to be either battery or line powered, are small and easily located anywhere in the home. The individual beacons do not have an assigned function under one embodiment. This allows for simple activation and placement. Under one embodiment, beacons send unique identification and health status only (i.e. battery life). Under alternative embodiments, beacons may also transmit minimum and maximum signal strength values and other functional parameters.

The systems and methods described herein include providing pet collar devices. Under an embodiment a pet wears a collar that is designed to receive beacon transmissions, and act upon and/or store the data transmissions. Pet collar devices may also transmit beacon configuration data and summarized collected data from all monitored beacons to one or more smartphone receivers. The collar is also capable of providing positive and negative reinforcement as necessary utilizing a number of different stimulation techniques.

Under one embodiment, beacons comprise Bluetooth® Low Energy beacons. Under alternative embodiments, beacons comprise Bluetooth Low Energy peripherals capable of RF connection. Further, collars may comprise Bluetooth low energy enabled devices that function in a manner analogous to beacons. Bluetooth low energy (BLE) is itself a wireless technology standard for personal area networks. BLE is targeted for very low power devices, i.e. devices that can run on a coin cell battery for months or years. Under an embodiment, Bluetooth enabled beacons/devices may comprise Bluetooth integrated circuit implementations. Updates to embedded code of a Bluetooth enabled device may be accomplished through firmware over the air upgrades. Mobile device operating systems may natively support the Bluetooth low energy wireless communications protocol. Such operating systems include iOS, Android, Windows Phone and BlackBerry, as well as OS X, Linux, and Windows 8.

A smartphone application is described herein that is used to set up, and configure the in-home detection/monitoring system and configure its components. The smartphone application may also be used to monitor and control beacons and/or collar devices and upload monitored data. As one example, the smart phone application, when in range of either a beacon or a collar device may receive data from such devices, collect the data and/or store the data. The smart phone application may also cause action by a device such as the collar or any beacon, manually or automatically. As further described below, the application may wirelessly signal the collar device to apply a corrective action, i.e. apply a stimulus to the corresponding pet. When configuring the system, the application may provide a simple user interface for configuring the system, its components and their functionality.

It should be noted that beacons, the pet collar device(s) and mobile devices may both transmit and receive data. Accordingly, each such component/device may serve a dual function of transmitting and receiving/collecting data as further described below. In the examples provided below, beacons and pet collar devices are Bluetooth enabled but embodiments are not so limited. Further in the examples provided below an operating system of a mobile device (running a smartphone application of the system described herein) natively supports Bluetooth communications. Such operating system also natively supports any other communications protocols as they become available.

Assume that a user implements the tracking/monitoring system within a one bedroom apartment premises/home. Under such embodiment, FIG. 1 shows a home premises featuring a plurality of beacons 110-170 distributed by owner/user throughout the premises. FIG. 1 shows a beacon 120 placed in a bathroom of the home. FIG. 1 shows a beacon 130 placed in a bedroom of the home. FIG. 1 shows a beacon 110 placed at a front door of the home. FIG. 1 shows a beacon 140 placed at a living room window of the home. A beacon 170 may also be placed in a kitchen of the home. It is of course possible to place a beacon just about anywhere in, or around, the premises including in proximity to the pet's bed (beacon 160), food/water bowl (beacon 150) or other locations that may require monitoring, e.g. pet doors, furniture, outlets, etc. The dotted circles indicate the RF energy emitted from each beacon. A solid circle 190 indicates a range or threshold distance from each beacon configured be an "action" or "threshold" distance as further described below.

Figure 2:
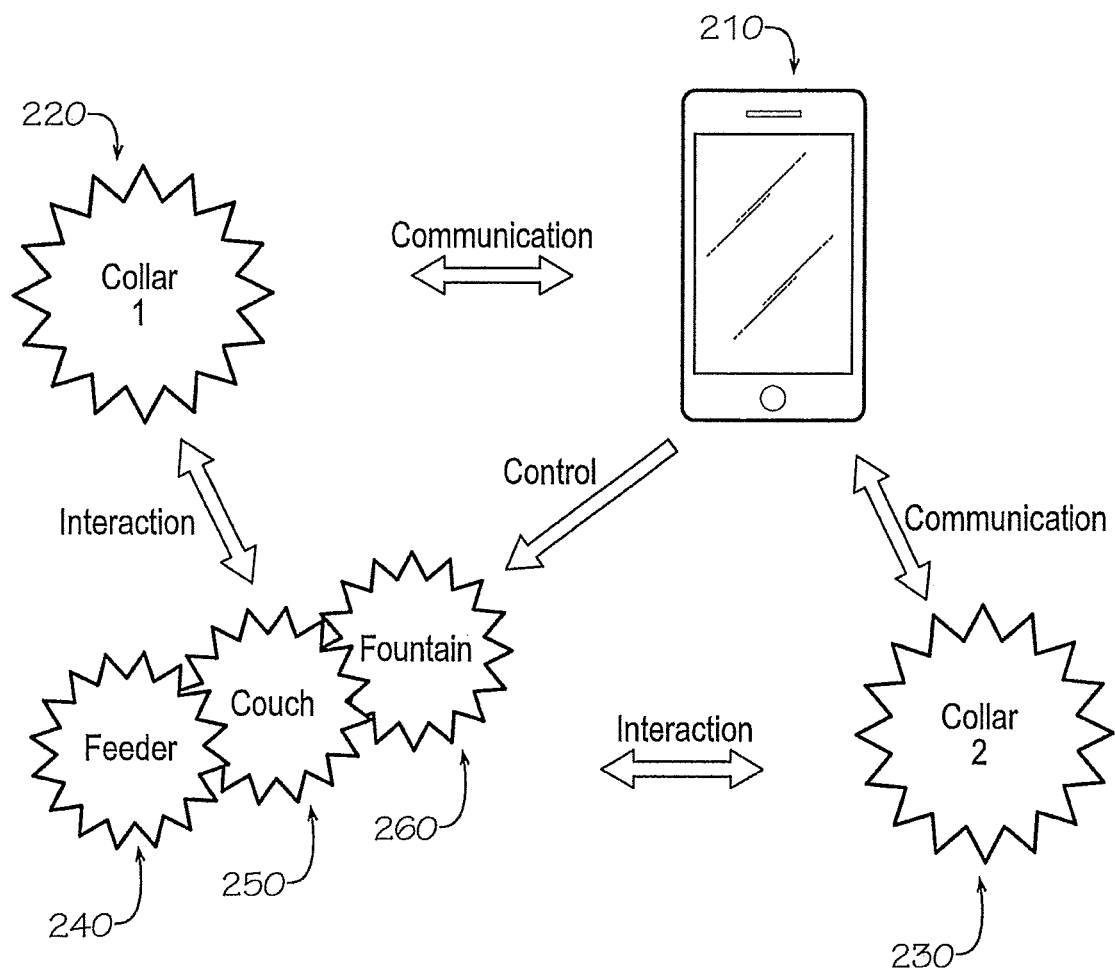
FIG. 2 shows the components of a monitoring system, under an embodiment.

FIG. 2 shows the components of a monitoring/tracking/detection system under an embodiment. FIG. 2 shows mobile device 210 running a smartphone application. The smartphone application is communicatively coupled to collar devices 220, 230. The smartphone application may transmit data to and control certain functions of the collar devices 220, 230 as further described below. The smartphone application may also receive data from collar devices as further described below. FIG. 2 shows collar devices 220, 230 communicatively coupled to beacons 240, 250, 260. The collar devices receive data periodically transmitted by beacons 240, 250, 260 and otherwise communicate with beacons 240, 250, 260 as further described below. The smartphone application 210 may assign certain functionality directly to beacons 240, 250, 260 and otherwise communicates with beacons as further described below.

As seen in FIG. 1, the beacons are indicated by dots located in select areas in a one-bedroom apartment, for example. A Bluetooth enabled beacon may periodically transmit data including a unique identification number. A Bluetooth enabled device, e.g. the collar device described herein, may receive the periodically transmitted data, extract the identification number and estimate the transmission's signal strength (i.e. received signal strength indication or "RSSI"). The collar device may then use the signal strength to estimate a distance from collar device to the transmitting beacon. The collar may be further assisted with its ranging calculation by utilizing calibration data contained within the beacon message. Further, the collar device itself periodically transmits data including a unique identification number. Under one embodiment, the collar device cycles between "transmission" and "listening" modes. As one example the collar device may periodically transmit data during a "transmission" period and then simply receive incoming signals from in range beacons/devices during a "listening" period. The collar may shift between "transmission" and "listening" periods in five second intervals. Under one embodiment, beacons similarly shift between transmission and listening modes.

Figure 3:
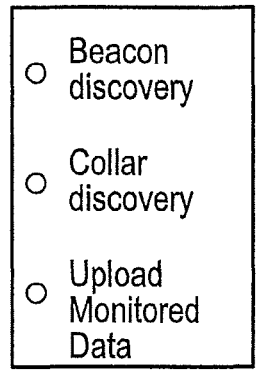
FIG. 3 shows an application interface providing discovery options, under an embodiment.

Under one embodiment, the smartphone application may provide an "easy to use" configuration interface. A pet owner may initiate the application on a smartphone and walk through a set up procedure using the configuration interface. For example, such interface of the application may provide click through buttons for "beacon" and "collar" discovery modes as seen in FIG. 3. The user may under this embodiment select "beacon" discovery mode. The interface may then prompt the user to bring the smartphone device in proximity to a transmitting beacon, i.e. within transmission range of a beacon. In beacon discovery mode, the application may use one or more mobile device operating system APIs to detect incoming Bluetooth transmissions. The application and mobile device detect the periodically transmitted beacon signal and identify/store its unique identification number. The mobile device may use strength of incoming signal to estimate a distance from the beacon. Under one embodiment, the application may only enable availability of discovery mode in close proximity to the transmitting beacon. The user may repeat this process for each and every beacon that the user wishes to deploy in the premises. In this manner, the application learns the identification number of each beacon deployed in the premises.

Continuing with this configuration example, a user runs the same application on the user's smart phone to configure the collar device for operation. As indicated above, an interface of the application may provide click through buttons for "beacon" and "collar" discovery modes as seen in FIG. 3. The user may under this embodiment select the "collar" discovery mode. The user brings the smartphone device in proximity to the pet collar device, i.e. within transmission range of the collar. In collar configuration mode, the application may use one or more mobile device operating system APIs to detect incoming Bluetooth transmissions originating from the collar device. The application and mobile device detect the periodically transmitted signals from the collar device and identify its unique identification number. The mobile device may use strength of incoming signal to estimate a distance from the collar device. Under one embodiment, the application may only enable availability of collar device discovery mode in close proximity to the collar device. The user may repeat this process for each and every collar device that the user wishes to deploy in the premises. In this manner, the application learns the identification number of each collar device deployed in the premises.

In this manner, the application may learn the unique identification number of all premises beacons and the pet collar devices. It should be noted that FIG. 3 provides a separate interface for discovery of beacons and collar devices. However, the discovery mode interface may be integrated into the workflow of beacon/collar configuration interfaces shown in FIGS. 4 and 6 and further described below. Note also that FIG. 3 provides Upload Monitor Data allowing the option to trigger upload of data collected by collar device to the smartphone.

A user may use the smartphone application to configure the collar (or collars) for operation, i.e. to configure "collar defined" functions or enable recognition of specific "tag defined" beacons. The collar itself performs a set of "active" and/or "passive" functions. Proximity to a beacon triggers one or more such functions as defined by the user with respect to the particular beacon. In other word, for each deployed beacon the user defines a collar implemented function triggered by the collar's entry into a defined proximity of a particular beacon.

Figure 4:
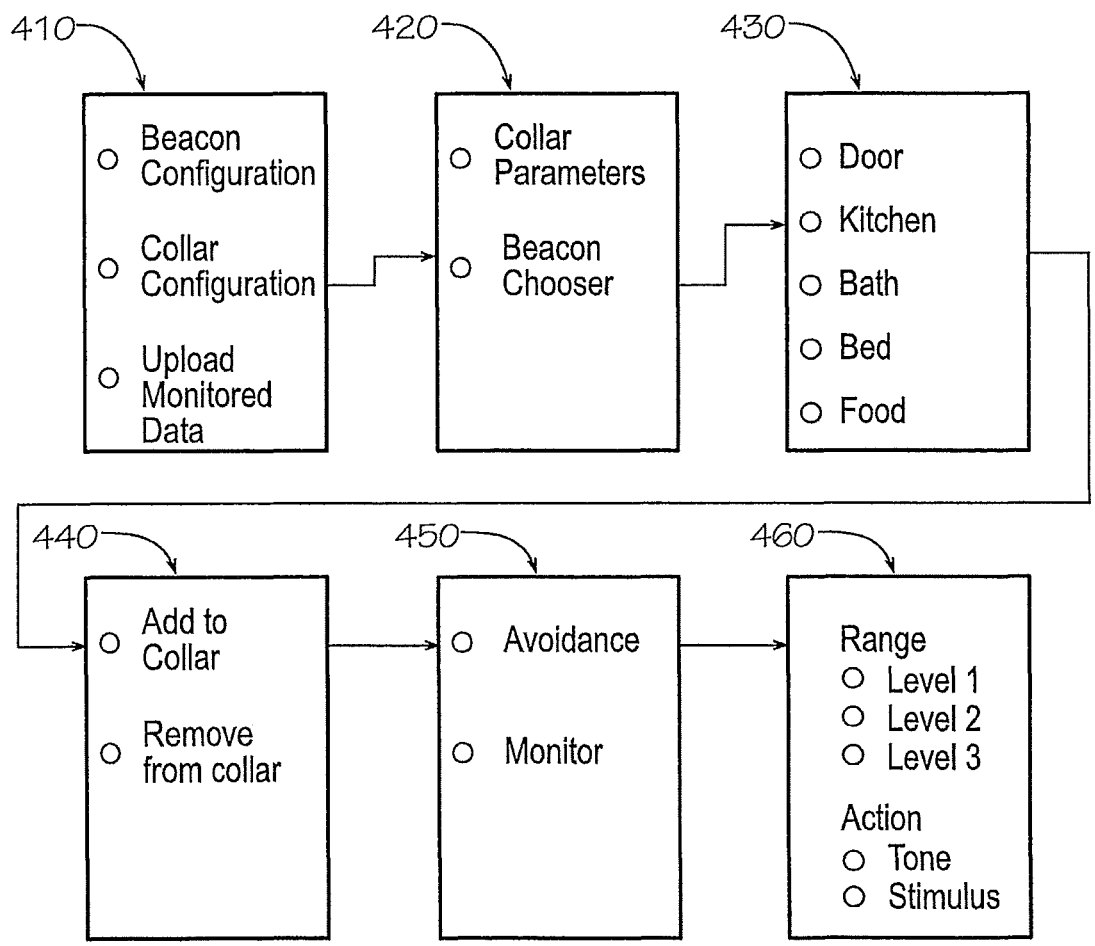
FIG. 4 shows an application interface providing configuration options, under an embodiment.

FIG. 4 shows an interface allowing a user to configure collar defined functions with respect to specific beacons. This system of this embodiment comprises a single collar and multiple beacons. Screen 410 shows a Beacon Configuration option (described below with respect to FIG. 6), a Collar Configuration option, and an Upload Monitor Data option. (The Upload Monitor Data Option of screen 410 provides the option to trigger upload of data collected by collar device to the smartphone). A user selects under one embodiment the Collar Configuration option and is presented with screen 420. At this screen 420 a user may select Collar Parameters or Beacon Chooser. The Collar Parameters option introduces an interface (not shown) for configuring functional parameters of the collar such as correction level. A user selects under an embodiment Beacon Chooser and proceeds to screen 430 which lists the beacons available within the system (e.g. door, kitchen, bath, bed, food). The user selects the kitchen beacon and is provided a choice at screen 440 between Add to Collar and Remove from Collar. The user may select Add to Collar to associate the kitchen beacon with the collar device. (The user may also select Remove from Collar to dissociate from the collar device a previously assigned beacon). After associating the kitchen beacon with the collar device, the user sees screen 450 featuring Avoidance and Monitor options. A user may assign the kitchen beacon an Avoidance function or a Monitor function. After selecting Avoidance, the user manipulates interface selections (at screen 460) to assign the collar a stimulus function when the collar is within a selected range (Level 1) of the beacon. Specifically the user selects a negative stimulus (applied by the collar) as an avoidance function and designates a corresponding range. The application interface may provide various stimulus functions (tone, stimulus, scent, etc.) and one or more ranges. Range Level 1 for example indicates close proximity to a beacon. Range Level 2 and Range Level 3 represent enlarged threshold distances. After selecting range and function, the user may be presented with another screen (not shown) allowing user to designate permitted access times, e.g. times during which the collar does not apply the designated function when the collar device in within the designated range. Embodiments are not limited to the functions and ranges described in FIG. 4. In this example, the user simply directs the collar to perform an avoidance function when the collar is within a near range threshold distance of the beacon. Once the configuration selections are complete for a collar/beacon combination, the application may prompt the user to bring the application in proximity to the collar device. The application may then transmit such configuration data to the pet collar device which uses the data to build/maintain a database which associates actions/functions with beacons (and corresponding unique identification numbers and permitted times). In this manner a user may assign functions to the collar with respect to each beacon within the system.

Figure 5:
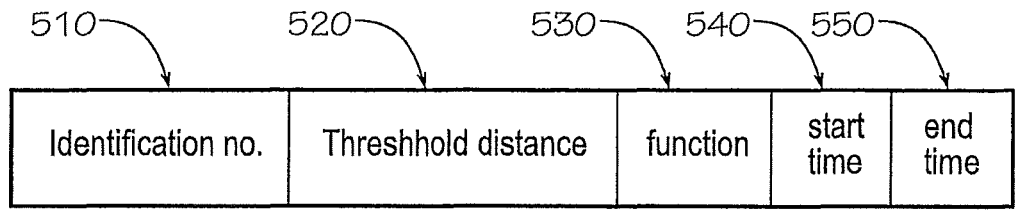
FIG. 5 shows a representative database entry of a database stored in a collar device, under an embodiment.

FIG. 5 shows a representative entry in a database which associates beacon identification number 510 with an avoidance function 530 and threshold distance 520. The representative database entry also includes start time 540/end time 550 of the configured function. Such database may associate values using a relational database scheme.

Continuing with this example, an operational pet collar device approaches the particular beacon and crosses over the configured threshold distance. During this event, the particular beacon simply transmits is unique identification number. The collar device receives the signal, identifies the unique identification number, and uses signal strength of the transmission to estimate a distance to the beacon. The collar device then uses the identification number to perform a database lookup to determine the assigned collar function with respect to the beacon (e.g., a negative stimulus) and conditions for its performance (e.g. location of the collar device within a certain threshold distance and permitted time of performance). In this example, the collar determines that the function is delivery of stimulus and also resolves that the estimated distance from collar to beacon is less than the selected threshold distance (via comparison of estimated distance with designated threshold distance). Therefore, the collar device delivers the avoidance stimulus to the pet wearing the collar device. It should be noted that threshold distance may comprise distance from a location or a range of such distances (including an upper and lower boundary).

In the example above, the assigned function comprises a user/collar defined function. In other words, a user may assign functions to collar/beacon combinations. For example, a user may wish to prevent a pet from jumping on the user's couch. Therefore, the user may assign a beacon located near the couch an avoidance function, i.e. assign an avoidance function to a collar with respect to such beacon. However, a user may simply wish to know how often a pet visits a water bowl in daytime hours while the user is away from the premises, i.e. the user may simply wish to track the location of a pet. Accordingly, a user may assign a beacon located near the water bowl a tracking function, i.e. assign a tracking function to a collar with respect to such beacon. The user then assigns the collar device the tracking function via the application in the same way the avoidance function is assigned (as described above). When the pet collar device is within a threshold distance of the beacon (and once the collar device processes conditions for performance of the assigned function based on beacon/function/distance/time parameters), the pet collar device simply logs location data, e.g. the occurrence of a threshold crossing, the time of a threshold crossing, duration of pet's proximity to a beacon, etc.). The tracking beacon may under an embodiment also administer a positive reinforcement such as a positive tone if so configured by the user.

The flexibility of the system is evident in view of a second pet collar device. Within the same monitored premises, the configuration process described above may be used to assign functions to a second collar device with respect to the same set of beacons. This set of functions may be entirely different than those assigned to the first collar. This is possible due to the fact that beacons merely transmit identification numbers while the collar devices detect/extract the identification numbers and then resolve/perform a user defined function based on configuration data stored in a collar specific database.

Figure 6:
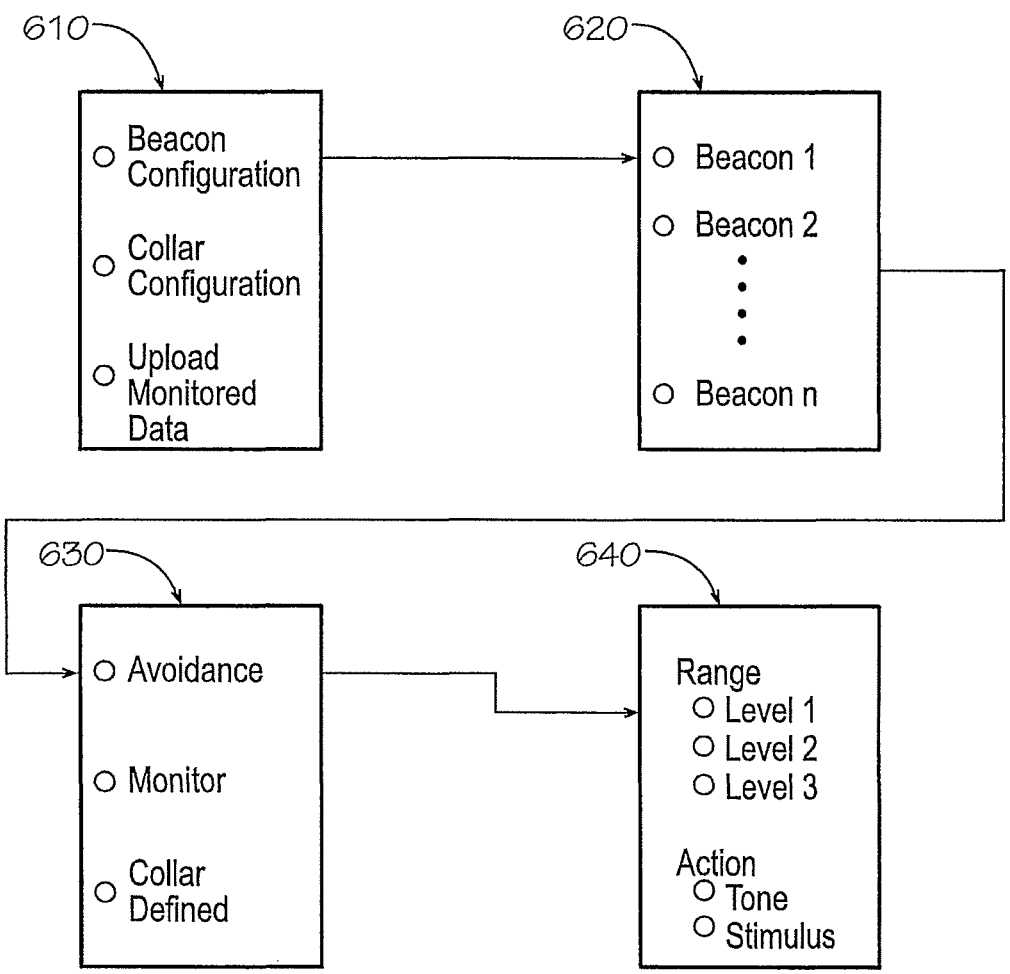
FIG. 6 shows an application interface providing configuration options, under an embodiment.

In contrast to "user defined" functions, a user may also dedicate a specific beacon to a particular task. For example, a user may use the application interface during setup to assign an avoidance function to a beacon directly. An example of directly configuring a beacon defined function using a smartphone application is provided below. A user initiates the smartphone application which under one embodiment provides an interface for assignment of functions directly to beacons. FIG. 6 shows a screen 610 featuring Beacon and Collar Configuration options as well as a Monitor Data option. For example, a user may select the Beacon Configuration option shown in FIG. 6. The interface may then present at the next screen 620 all discovered beacons, i.e. up to "n" number beacons discovered via the process described above and as seen in FIG. 6. (It should be understood that Beacons 1-n may be replaced by the names of the monitored locations, e.g. kitchen, door, window, etc.). A user then selects a particular beacon (e.g. beacon 2) and then views configuration options at screen 630 for the pet collar with respect to the selected beacon. Screen 630 shows Avoidance and Monitor options which represent options to assign an Avoidance or Monitor function to the beacon. (The Collar Defined option provides the option to designate a beacon as collar defined which means that the beacon's interaction with a collar device is governed by configuration data maintained by the collar device as described above with respect to FIG. 4). The user may under an embodiment designate an Avoidance function at screen 630. The user is then presented at screen 640 with range and action options as seen in FIG. 6. The user manipulates interface selections to assign the collar a stimulus function when the collar is within a selected range (Level 1) of the beacon. Specifically the user selects a negative stimulus (applied by the collar) as an avoidance function and designates a corresponding range. The application interface may provide various stimulus functions (tone, stimulus, scent, etc.) and one or more ranges. Range Level 1 for example indicates close proximity to a beacon. Range Level 2 and Range Level 3 represent enlarged threshold distances. After selecting range and function, the user may be presented with another screen (not shown) allowing user to designate permitted access times, e.g. times during which the collar does not apply the designated function when the collar device in within the designated range. Embodiments are not limited to the functions and ranges described in FIG. 6. Once the configuration selections are complete for a beacon, the application may prompt the user to bring the application in proximity to the beacon. The application may then transmit such configuration data (including function data, distance data, and permitted times data) to the beacon. The beacon encodes the particular configuration data into packets for inclusion in the beacon's periodic transmissions. Accordingly, the beacon periodically transmits both its identification number and the configuration data to devices within its range. In this manner a user may assign a function directly to each beacon within the system. Under an embodiment, the application also transmits the unique identification number of the particular configured beacon to the collar device. In this manner, the collar device may monitor incoming beacon transmissions and confirm that the beacon is part of the configured system under this embodiment.

As indicated above, a user may use the application interface during setup to assign an avoidance function to a beacon directly. During set up operations, the application transmits such configuration data to the specifically tasked beacon. (It should be noted beacons not only transmit data, they may also receive and store data from other beacons or devices). The transmitted data includes "function data" (which encodes the particular function in data packets for inclusion in the beacon's periodic transmissions), threshold distance (and permitted time data under an embodiment). The application may also send the beacon's identification number to the collar device which stores such information. Accordingly, the beacon periodically transmits its identification number, the function data, and a threshold distance (and permitted times under an embodiment) to devices within its range. Under this example, the pet collar device may approach the beacon transmitting the identification number and corresponding data. The collar device then extracts the identification number, the "function data", distance data (and permitted time data under an embodiment) and uses the signal strength of the transmission to estimate distance from the beacon. The collar device may match the identification number to stored beacon identification numbers to ensure that the particular beacon is part of the configured system, i.e., that the collar device should proceed. The collar device may then match "function data" with function type, e.g. avoidance, tracking, etc., using embedded code within a pet collar. Alternatively, a smartphone application may transmit such data to the collar device during set up operations. Under this example, the function data corresponds to an avoidance task, i.e. delivery of negative stimulus. The collar device then resolve whether the device is within the designated threshold distance (and within appropriate time interval under an embodiment). If so, the collar device executes the assigned function, i.e. delivers the negative stimulus.

Figure 7A:
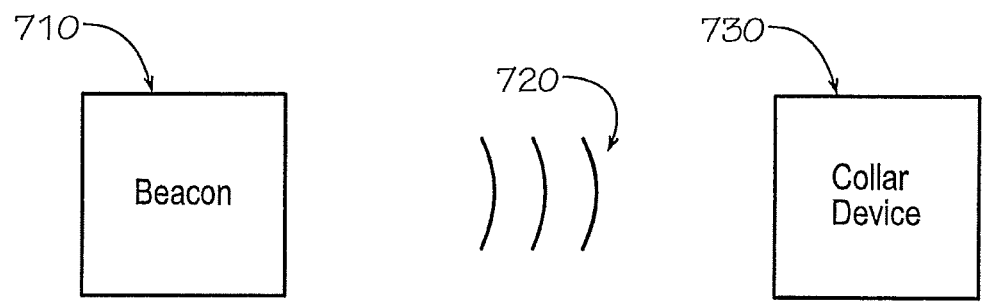
FIG. 7A shows a beacon defined interaction between beacon and collar device, under an embodiment.

FIG. 7A shows a beacon defined embodiment of beacon/device functionality. Under this embodiment, the beacon 710 transmits 720 its identification number, a distance range (e.g., nearby range) and function data. (It should be noted that distance range may comprise distance from a location or a range of such distances including an upper and lower boundary). The collar devices uses signal strength to estimate distance from the transmitting beacon. The collar device 730 extracts function data (corresponding to negative stimulus) and distance range information from the signal. The collar device interprets the function data as a negative stimulus function, and if the collar device determines that the collar device is within a near range distance, then the collar device applies the negative stimulus. The collar device may also log the time/duration of the event along with corresponding identification number of the beacon.

Figure 7B:
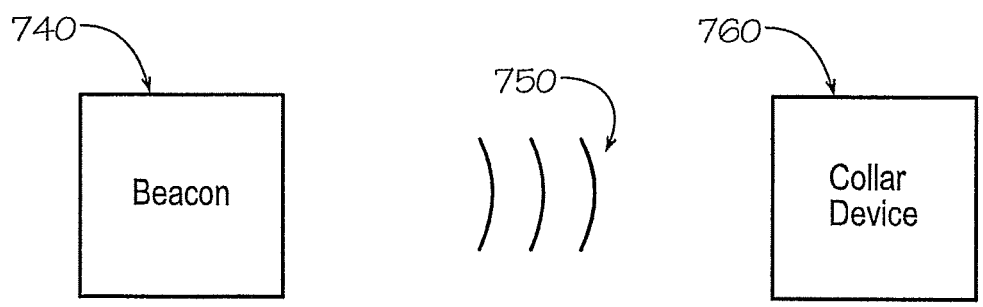
FIG. 7B shows a collar defined interaction between beacon and collar device, under an embodiment.

FIG. 7B shows a collar defined embodiment of beacon/device functionality. Under such embodiment, the beacon 740 (located near a couch) simply transmits 750 its unique identification number. The collar device 760 then detects the transmission, identifies the identification number and uses signal strength to estimate distance from the transmitting beacon. The collar device then uses the identification number to look up configuration data. Under this embodiment, such data comprises an avoidance function (i.e., negative stimulus), and a midrange distance. (It should be noted that distance range may comprise distance from a location or a range of such distances including an upper and lower boundary). If the collar device determines that the device is within a midrange distance, then the collar device applies the negative stimulus. The collar device may also log the time/duration of the event along with corresponding identification number of the beacon.

Figure 8A:
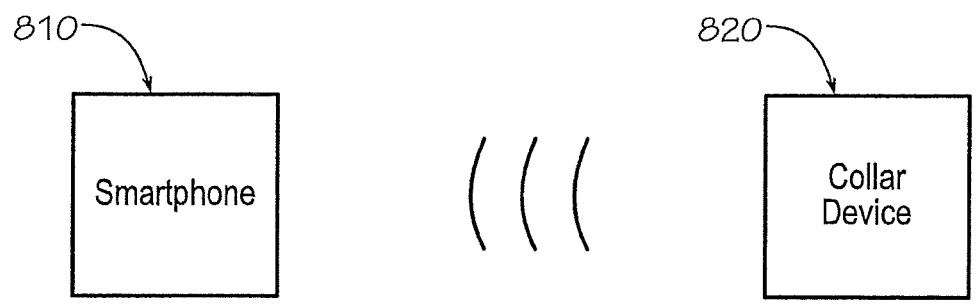
FIG. 8A shows a one way communication between smartphone and collar device, under an embodiment.
Figure 8B:
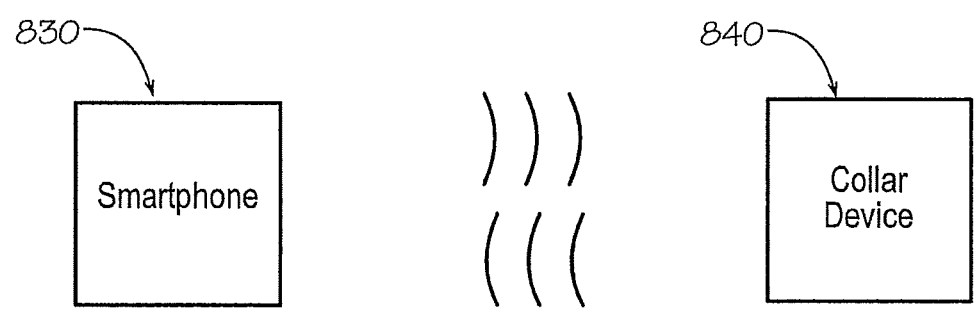
FIG. 8B shows two way communications between smartphone and collar device, under an embodiment.

FIG. 8A shows a collar device 820 transmitting data to a smartphone 810 under one embodiment. FIG. 8B shows two way communication between a collar device 840 and a smartphone 830 under one embodiment.

Under one embodiment, a home detection kit may ship with a collar and corresponding beacons. A user may first register the smart phone application with a company provided internet service. Registration may provide the application with the unique device identification numbers of the beacons and the collar(s). Alternatively, the application may discover identification numbers during configuration as described in detail above.

Under one embodiment, a pet owner/user deploys beacons in a home. The user simply locates beacons in areas of interest. The pet owner uses a collar, in conjunction with a smartphone application to assign "Avoid" and/or "Track" functions to collar/beacon combinations. As an example of assigning an "Avoid" function (using the procedures already described in detail above), a user first places a red sticker on a beacon. The user then approaches the beacon with a mobile device running the smartphone application. The application/device reads the unique identification of the beacon and reads receiver signal strength indication (RSSI) value. The application then communicates with the collar to assign collar a function of the particular beacon when the pet collar is within a set range of the beacon. If the pet collar comes within a configured distance of the particular beacon, the collar triggers a negative stimulus and stores the time of the event under an embodiment.

As an example of assigning a "Track" function (using the procedures already described in detail above), a user first places a green sticker on beacon. The user then approaches the beacon with a mobile device running the smartphone application. The application/device reads the unique identification of the beacon and reads receiver signal strength indication (RSSI) value. The application then communicates with the collar to assign collar a function of the particular beacon when the pet collar is within a set range of the beacon. If the pet collar comes within a configured distance of the particular beacon, the collar will log the occurrence of the event and/or emit a positive reinforcement stimulus under an embodiment. The collar may also store the time of the event.

As the pet wearing the collar moves about the home, the collar collects data while controlling the pet's whereabouts through stimulus events triggered by proximity to "red" beacons and tracked events triggered by proximity to "green" beacons. When the collar is within range of the smart phone application, the collar transmits all collected/queued data to the application which may then display such information. A user may also deliver immediate Avoid/Track commands to the collar.

Figure 9:
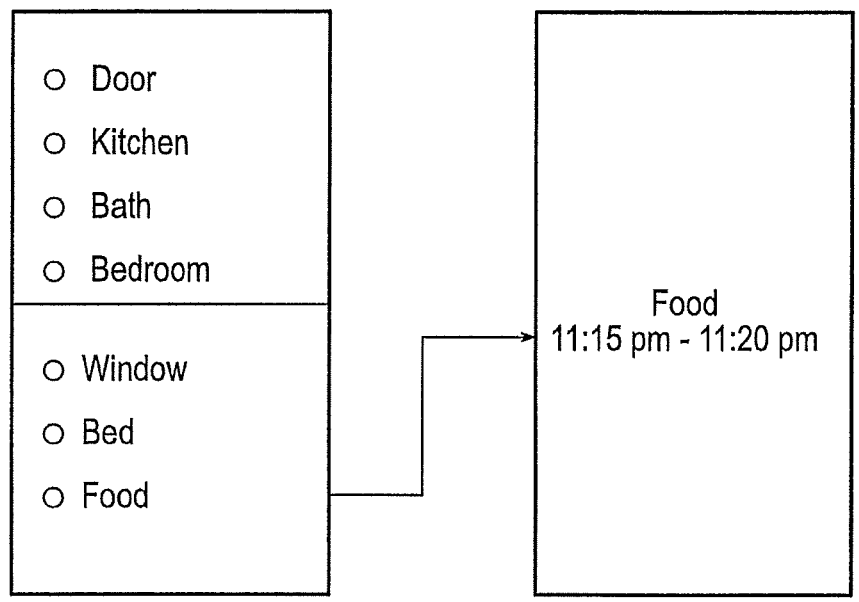
FIG. 9 shows an application interface providing user a selection among multiple beacons, under an embodiment.

FIG. 9 shows an application interface allowing user a selection among beacon locations. A user may select "Food" which then directs user to another page featuring tracking data. In this example (as seen in FIG. 9), the interface shows that the user's pet was within a configured range of the pet's water bowl from 11:15-11:20 pm.

Figure 10:
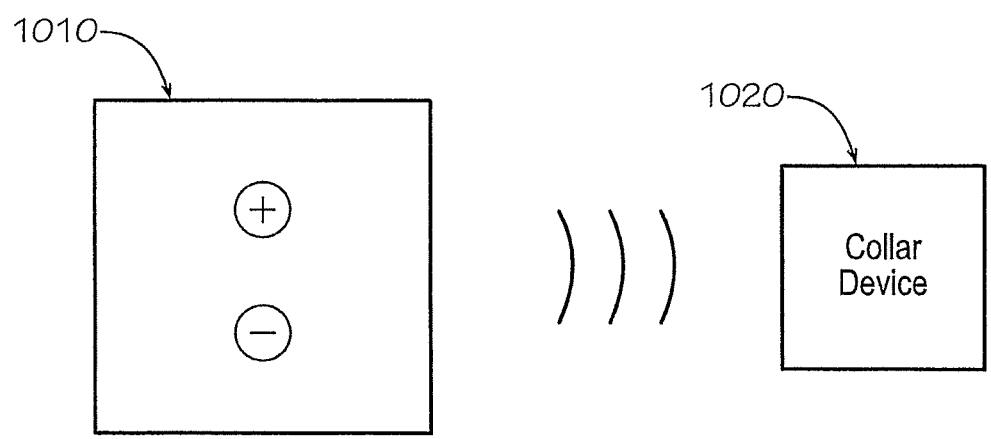
FIG. 10 shows a remote training application interface, under an embodiment.

FIG. 10 shows a "Remote Trainer" interface page of an application running on a smartphone 1010. A user may select the "+" button to direct the collar 1020 to administer a positive stimulus. A user may select the "−" button to direct the collar 1020 to administer a negative stimulus.

Under one embodiment, Bluetooth LE modules are used in the beacons and collars of the systems and methods described above. Alternatively, unique RF beacons may be specially designed for this detection/tracking/monitoring system described herein.

Under one embodiment, one or more of a pet collar device, a beacon, and smartphone may be communicatively coupled via Wi-Fi or WPAN communications protocols to a local router to provide a communicative coupling with wide area networks, metropolitan area networks and with the internet in general. Each such device therefore is communicatively coupled to a remote cloud computing platform comprising one or more applications running on at least one processor of a remote server. Accordingly, the collar/beacons/smartphone may transmit data to and/or receive data from a cloud computing platform.

Under one embodiment, beacons may comprise a green and red side. If placed with green side up, the beacon may be automatically configured as a "Track" location. If placed with red side up, the beacon may be automatically configured as an "Avoid" location.

It is understood that the systems and method described herein are merely illustrative. Other arrangements may be employed in accordance the embodiments set forth below. Further, variations of the systems and method described herein may comply with the spirit of the embodiments set forth herein.

Figure 11:
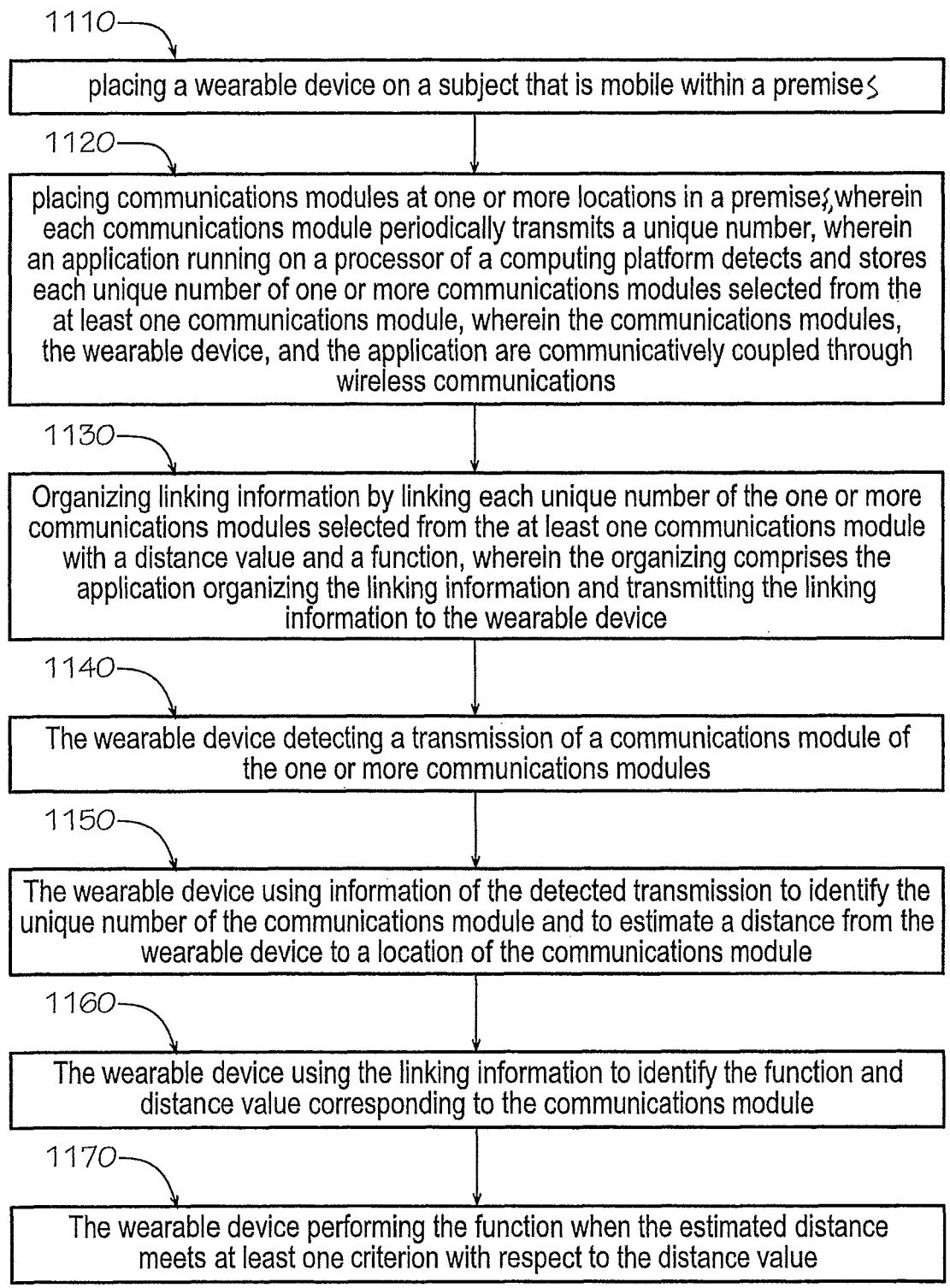
FIG. 11 shows a method of monitoring a subject in a premises, under an embodiment.

FIG. 11 comprises a method monitoring a subject in a premises, under an embodiment. Step 1110 includes placing a wearable device on a subject that is mobile within a premises. Step 1120 includes placing communications modules at one or more locations in a premises, wherein each communications module periodically transmits a unique number, wherein an application running on a processor of a computing platform detects and stores each unique number of one or more communications modules selected from the at least one communications module, wherein the communications modules, the wearable device, and the application are communicatively coupled through wireless communications. Step 1130 includes organizing linking information by linking each unique number of the one or more communications modules selected from the at least one communications module with a distance value and a function, wherein the organizing comprises the application organizing the linking information and transmitting the linking information to the wearable device. Step 1140 includes the wearable device detecting a transmission of a communications module of the one or more communications modules. Step 1150 includes the wearable device using information of the detected transmission to identify the unique number of the communications module and to estimate a distance from the wearable device to a location of the communications module. Step 1160 includes the wearable device using the linking information to identify the function and distance value corresponding to the communications module. Step 1170 includes the wearable device performing the function when the estimated distance meets at least one criterion with respect to the distance value.

Systems and methods for monitoring a subject in a premises are described above in detail. In accordance with such disclosure, FIG. 2 shows one embodiment of a system for monitoring/tracking/detecting activities of a subject within a premises. FIG. 2 shows a mobile device 210 running a smartphone application. The smartphone application is communicatively coupled to collar devices 220, 230. The smartphone application may transmit data to and control certain functions of the collar devices 220, 230 as described above. The smartphone application may also receive data from collar devices as described above. FIG. 2 shows collar devices 220, 230 communicatively coupled to beacons 240, 250, 260. The collar devices receive data periodically transmitted by beacons 240, 250, 260 and otherwise communicate with beacons 240, 250, 260 as described above. The smartphone application 210 may assign certain functionality directly to beacons 240, 250, 260 and otherwise communicates with beacons as described above.

Under the embodiment described above, a monitoring/tracking/detection system includes one or more collar devices, one or more beacons, and at least one smartphone running an application and providing user interaction with such system. However, an additional embodiment of the monitoring/tracking/detection system may include additional sensors or devices that proactively monitor and manage the health and well being of a subject under observation within the protected/monitored premises. These additional sensors/devices include collar device sensors, environmental sensors, and action or activity sensors. However, it should be noted that these additional sensors/devices of a monitoring/tracking/detection system may represent one or more components from any single sensor/device category or from any combination of sensor/device categories.

Collar Device Sensors

The collar device itself may include sensing devices for monitoring the health and well being of a subject wearing the collar device. These sensing devices may monitor biological and physiological metrics of a subject wearing the collar device. The sensing devices may also monitor motion and activity parameters of a subject wearing the collar device. The subject may comprise an animal but embodiments are not so limited. Under this embodiment, the collar device includes one or more of the following monitoring/sensing devices:

- the collar device may include a heart rate sensor for monitoring heart rate.
- the collar device may include an Electrocardiogram to monitor a heart's electrical activity (EKG or ECG).
- the collar device may include one or more blood pressure sensors to monitor blood pressure levels.
- the collar device may include one or more respiration rate sensors for monitoring respiration rates.
- the collar device may include one or more temperature sensors for monitoring body temperature.
- the collar device may include an accelerometer and/or gyroscope in order to monitor activity levels and activity types.
- the collar device may include one or more acoustic sensors or one or more sensors for detecting frequency, amplitude, and origin of audio signals.
- the collar device may include one or more piezoelectric sensors and/or transducers. Such sensor/transducers are devices that uses the piezoelectric effect to measure changes in pressure, acceleration, temperature, strain, or force by converting them to an electrical charge.
- the collar device may include one or more lightning sensors for the detection of lightning.

It should be noted that a collar device is not limited to traditional configurations of a collar. Rather, a collar device may comprise any wearable device that may position sensor devices at various physical locations on the subject wearing the device. Further, the collar may be communicatively coupled with one or more of the sensors described above and which are also positioned at various physical locations on the subject external to the collar device. As just one example, a transducer may located against the neck of an animal and may detect a bark, howl, or other sounds generated by the animal.

Environmental Sensors

Environmental sensors may be distributed throughout the premises of a monitoring/tracking/detection system. These sensors monitor and detect environmental parameters of a premises. Environmental sensors may include temperature sensors, moisture sensors, humidity sensors, air pressure sensors and/or air quality condition sensors. Environmental sensors may include one or more acoustic sensors or one or more sensors for detecting frequency, amplitude, and origin of audio signals. Environmental sensors may include one or more piezoelectric sensors and/or transducers. Such sensor/transducers are devices that uses the piezoelectric effect to measure changes in pressure, acceleration, temperature, strain, or force by converting them to an electrical charge. Environmental sensors may include one or more lightning sensors for the detection of lightning However, a monitoring/tracking/detection system may clearly incorporate fewer or additional numbers and types of environmental sensors. Such environmental sensors may be directly attached to or incorporated within a beacon. Under this embodiment, environmental sensors are electronically connected to a beacon. Alternatively, environmental sensors may be located in proximity to beacons. Under this embodiment, environmental sensors may be in wired or wireless communication with beacons. Under another embodiment, environmental sensors may be located in a position to detect an overall condition of an environment. Under the embodiments described above, environmental sensors (i) may communicate directly with a collar device or (ii) may communicate with a collar device through an intermediate beacon device. Environmental sensors are Bluetooth enabled under an embodiment and capable of Bluetooth Low Energy protocol communications.

Activity Devices

Activity or action devices may be distributed throughout the premises of a monitoring/tracking/detection system. Under one embodiment, an activity device may be electrically connected to or incorporated within another device. For example, activity devices may represent switches which control the operation or function of yet other devices, e.g. the flow of water in a dispensing device, the management of food volume/type in a food dispensing device, etc. Further, an activity device may represent a switch that monitors thermostat levels. As another example, an activity device may itself comprise a toy or audio playback device. Such devices are Bluetooth enabled under an embodiment and capable of Bluetooth Low Energy protocol communications.

Further, collar devices and/or activity devices described herein may include a microphone for emitting signals or for receiving, interpreting, and performing audible instruction using voice recognition. It should be noted that any of the sensors described herein may be equipped with transceiver and may be communicatively coupled to one or more transceiver enabled microphones. Accordingly, such sensors may be subject to voice control, i.e. may receive instructions originally received by one or microphones. The disclosed microphones may under one embodiment interpret such instructions using voice recognition and then forward such instructions to one or more communicatively coupled sensors.

Of course it should be noted that fewer or additional numbers and/or types of collar device sensors, environmental devices and activity devices may be included in the monitoring/tracking/detection system of an embodiment.

Figure 12:
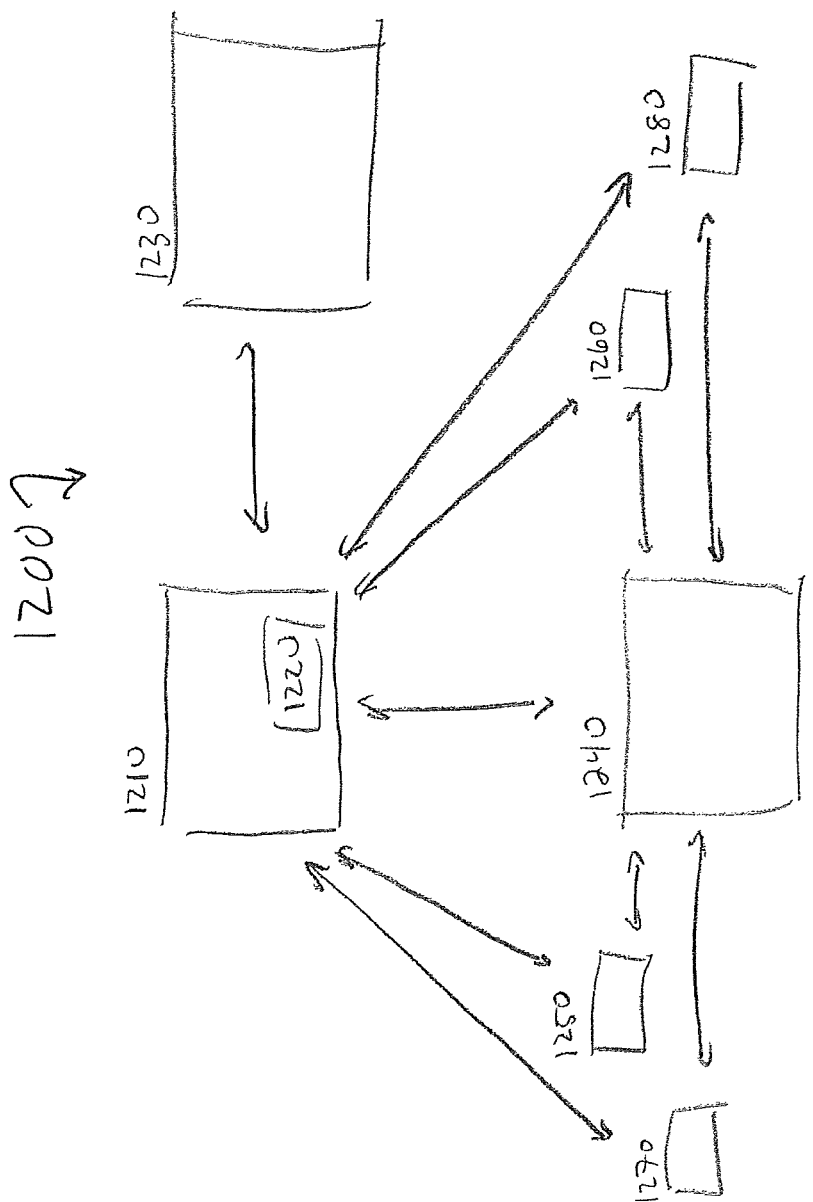
FIG. 12 shows components of a monitoring system, under an embodiment.

FIG. 12 shows the components of a monitoring/tracking/detection system including the additional devices and sensors that provide pro-active health and well being functionality under one embodiment. The wireless network 1200 of FIG. 12 comprises under one embodiment a collar device 1210, a beacon device 1240, and a mobile device 1230 running a smartphone application. The collar device includes collar device sensors 1220. FIG. 12 shows environmental sensor 1250 communicatively connected with beacon 1240 and environmental sensor 1260 communicatively connected with beacon 1240. FIG. 12 also shows activity device 1270 communicatively connected with beacon 1240 and activity device 1280 communicatively connected with beacon 1240. FIG. 12 also shows that environmental sensors 1250, 1260 and activity devices 1270, 1280 may be directly communicatively connected with a collar device 1210 and may also communicate with the collar device 1210 through beacon 1240. The mobile device of FIG. 12 is communicatively coupled with components 1240, 1250, 1260, 1270, and 1280 through wireless network 1200.

Note that FIG. 12 shows the components of a monitoring/tracking/detection system that includes a single beacon and a single collar device. Of course, such system may include a plurality of beacons and a plurality of collar devices. Further note that FIG. 12 discloses environmental sensors positioned in a location remote to the beacon. Alternatively, the beacon itself includes one or more environmental sensors. Under this embodiment, such environmental sensors are electronically connected to and incorporated within the beacon. Further, FIG. 12 shows a monitoring/tracking/detection system featuring collar device sensors, environmental sensors, and activity devices. However, a monitoring/tracking/detection system may include any individual or combined use of sensors/devices from any sensor/device category (i.e. collar, environmental, or activity) or any combination of categories.

Operation of a "pro-active health and well being" monitoring/tracking/detection system involves the interaction of Bluetooth enabled collar device sensors, environmental sensors and/or activity devices. As indicated above, the collar device itself includes sensors that monitor biological, physiological, and motion parameters of a subject roaming the environment of a monitored premises. The environmental sensors simultaneously monitor and detect the environmental conditions of the premises. Each environmental sensor then periodically transmits such monitored/detected data. Each such environmental sensor may pair (or be associated) directly with a corresponding beacon, i.e. a particular beacon may detect, receive and store data periodically transmitted by an associated environmental sensor data. The beacon may then bundle the received sensor data into its own periodic broadcast transmissions. Recall from the discussion above that beacons and collar devices interact within a premises under a collar defined mode or beacon defined mode. Under a collar defined mode, a beacon periodically transmits an identification number (along with other data). A collar moving within communications range of a beacon receives the transmission and extracts the identification number. The collar device then uses internal data tables to match the identification number with avoidance/interaction functions. Alternatively, the beacon may itself determine the behavior of the collar device, i.e. the beacon may transmit identification and function data to an "in range" collar device. Under either configuration, a beacon may simply incorporate collected environmental sensor data into its periodic transmission such that "in range" collar devices in turn detect environmental sensor data associated with a particular beacon. Alternatively, each environmental sensor may periodically transmit data for detection by any "in range" collar device roaming within the wireless communications network of the overall monitoring/tracking/detection system. Environmental sensor transmissions may under an embodiment include unique identification numbers for use by components of a monitoring/tracking/detection system Environmental sensors may be associated with particular beacons or may be positioned to monitor an overall environmental condition of a premises. In this manner, environmental sensors may monitor micro-environmental conditions near or with respect to particular beacons or macro-environmental conditions within a premises.

In operation of a "proactive health and well-being" monitoring/tracking/detection system, a collar device collects a wealth of information as it roams throughout the monitored premises. First, the collar device may collect data with respect to avoidance/tracking events (otherwise referred to herein as avoidance/interaction events) triggered by proximity to particular beacons. (Note that avoidance/tracking events and the logging of information related thereto are disclosed in great detail above). Second, the collar device includes one or more sensors for monitoring/tracking/detecting physiological and motion metrics associated with a subject wearing the collar. Third, the collar device detects and receives data from environmental sensors that are (i) distributed throughout the premises and/or (ii) located within a beacon. The collar device may collect and process avoidance/interaction data, collar device sensor data (including physiological and motion activity data of a subject wearing the collar), and/or environmental sensor data to determine particular needs. As just one example and as further described below, the combination of avoidance/interaction data, physiological condition data, and/or environmental sensor data may indicate that an animal wearing the collar is not eating or drinking appropriate quantities of food/water.

Based on a determination of need, i.e. the need to induce increased intake of food/water, the collar device may interact with action or activity devices distributed throughout the premises, i.e. the collar device may activate functional changes in activity devices in order to address the need. For example, an activity device may represent Bluetooth enabled switches which control the operation or function of yet other devices. For example, if the collar device determines a need to induce increased intake of water, the collar device may communicate with a Bluetooth enabled switch that toggles a fountain motor of a water bowl. The communication may activate the fountain motor in order to encourage drinking of water. Under this embodiment, the collar device is communicatively coupled to the activity device through the WPAN network described above with respect to FIG. 12. The collar device may exchange data directly with activity devices or may communicate with activity devices through beacons associated or paired with such activity devices.

As indicated above, a collar device may collect and process avoidance/interaction data, collar device sensor data (including physiological conditions and motion activity of a subject wearing the collar), and environmental sensor data to determine particular needs. It should be noted that a collar device may determine a need using any single type of data, i.e. avoidance/interaction, collar device sensor, and environmental, or using any combination of data types. Once a need is determined, the collar device may determine and direct functional changes of activity devices within the premises of a monitoring/tracking/detection system. The collar device may exchange data directly with action/activity devices or may communicate with action/activity devices through beacons associated or paired with such activity devices. Accordingly, data collection and analysis may be conducted by a collar device. However, data collection and analysis may also take place at a cloud computing level.

As described above with respect to FIG. 12, a pet collar device, beacons, smartphone, environmental sensor and activity devices may be communicatively coupled via WPAN compatible communications (e.g. Bluetooth communications protocols under an embodiment) to a local router or communications hub providing a communicative coupling with wide area networks, metropolitan area networks and with the broader internet in general. Each such networked device within the monitoring/tracking/detection system may therefore be communicatively coupled to a remote cloud computing platform comprising one or more applications running on at least one processor of a remote server. Accordingly, the collar/beacons/smartphone, environmental sensors, and/or activity devices may transmit data to and/or receive data from a cloud computing platform. Under this embodiment, a collar device may collect and forward avoidance/interaction data, collar device sensor data (including physiological conditions and/or motion activity of a subject wearing the collar), and/or environmental sensor data. In other words, a collar device may collect and forward such data to a remote application running on a remote computing platform which may then itself analyze the data to determine a particular need of a subject wearing the collar device. Once a need is determined, the remote application may determine and direct functional changes of activity devices within a premises of a monitoring/tracking/detecting system. The remote application may communicate with a collar device which then transmits function change information to activity devices to trigger actions designed to address the identified need (as described above). Alternatively, the remote application may communicate functional change information directly to beacons which then communicate with and control activity devices accordingly. Further, the remote application may communicate directly with activity devices.

As described above, the collar/beacons/smartphone, environmental sensors, and/or activity devices may transmit data to and/or receive data from a cloud computing platform. Under this embodiment, a collar device may collect and forward avoidance/interaction data, collar device sensor data (including physiological conditions and/or motion activity of a subject wearing the collar), and/or environmental sensor data. In other words, a collar device may collect and forward such data to a remote application running on a remote computing platform. The remote application may then transmit this data to an application running on a smartphone or other mobile computing platform. The smartphone application may then analyze the data to determine a particular need of a subject wearing the collar device. Once a need is determined, the smartphone application may determine and direct functional changes of activity devices within a premises of a monitoring/tracking/detecting system. The smartphone application may then transmit functional change information to the remote application running on at least one processor of a remote server.

Under one embodiment, the smartphone application determines a need based on any single type of data, i.e. avoidance/interaction, collar device sensor, and environmental, or based on any combination of data types. The smartphone application may present the user an interface alerting the user of any currently identified need. The interface may also recommend a course of action to address the need, i.e. recommend particular action or operation of an activity device to address the need. The user may select or ignore recommend courses of action. The smartphone application may then communicate function change information to the remote computing platform which may then process such information in a manner already described above.

The user may use the smartphone application to configure automated cloud computing platform or collar device responses to identified needs. As already indicated above, a collar device, remote computing platform, or smartphone application may analyze avoidance/interaction data, collar device sensor data, and/or environmental sensor data. A collar device, remote computing platform, or smartphone application may determine a need using any single type of data, i.e. avoidance/interaction, collar device sensor, and environmental, or using any combination of data types. In other words, a need may comprise any single instance or combination of avoidance/interaction data, collar device sensor data, and environmental data. The user may use the smartphone application to associate activity device action with defined instances or combinations of avoidance/interaction data, collar device sensor data, and environmental data. The smartphone application, collar device or remote computing platform may then automatically apply remedies, i.e. activity device action, upon detection/identification of corresponding needs.

The smartphone application may provide the user with remote activity device control. As opposed to automating activity device responses and as opposed to accepting or rejecting activity device recommendations, the user may simply manually control premises activity devices. As already indicated above (and further described in great detail below), the user may be alerted of premises activity, i.e. detected/identified needs, through a smartphone application interface. The user may then manually direct in premises activity devices to perform specific functions or operations in order to address the detected/identified need.

The following disclosure provides Use Case Examples of a "proactive health and well-being" monitoring/tracking/detection system. For purposes of providing the Use Case Examples, assume the collar device includes the following sensors for measuring biological and physiological metrics of a subject wearing the collar device: Heart Rate Sensor, Electrocardiogram, Blood Pressure Sensor, Respiration Rate Sensor and Temperature Sensor. Such devices indicate physiological conditions in real time. The collar device may also include an Activity Monitor (e.g. accelerometer and gyroscope) which indicates real time physical activity levels of the subject wearing the collar device. Further with respect to the Use Case Examples described below, assume that environmental sensors are distributed throughout a premises of a monitoring/tracking/detection system. With respect to the examples provided below, environmental sensors include temperature, moisture, humidity, air pressure and/or air quality condition sensors. In addition, activity devices are also distributed throughout the premises. Activity devices may control the function, operation, or performance of additional devices. For example, an activity device may control the level of a thermostat or a dispensing mechanism of a food/water dispenser. As already described in great detail above, a collar device (including collar device sensors), beacons, environmental sensors, and activity devices are communicatively coupled through a Wireless Personal Area Network (WPAN). Under this embodiment, the WPAN enables wireless communications among such devices using Bluetooth Low Energy communication protocols. It should be noted that Use Case Examples may include additional types and numbers of collar sensors, environmental sensors and activity devices as required by the particular example.

Use Case Example

The collar device receives, monitors and collects avoidance/interaction data, collar device sensor data (including physiological condition data and activity level data), and/or environmental sensor data. The collar device may combine a subset of physiological conditions, physical activity levels, environmental sensor data, and/or interaction events (with respect to food and water bowls) to determine if intake requirements are being met. If not, then . . .

the collar device may trigger a water dispensing device to encouraged drinking with the addition of flavorings;

the collar device may encourage drinking of water by activating a fountain motor;

the collar device may trigger dispensing of treats by food dispensing device to encourage eating.

Use Case Example

The collar device receives, monitors and collects avoidance/interaction data, collar device sensor data (including physiological condition data and activity level data), and/or environmental sensor data. Accordingly, the collar device may monitor the physical activity sensor to determine if too much or too little physical activity is occurring. If change is needed, then . . .

the collar device may active toys (i.e., activity devices) to encourage activity;

the collar device may communicate with temperature control devices to adjust temperature so as to encourage or discourage activity;

the collar device may activate audio playback devices to provide calming or stimulating environmental sounds, noises, tones, music, etc.

the collar device may communicate with activity devices that control opening/closing of doors, i.e. doors may be locked or unlocked to encourage or discourage physical activity in proximity to a given beacon.

Use Case Example

The collar device receives, monitors and collects avoidance/interaction data, collar device sensor data (including physiological condition data and activity level data), and/or environmental sensor data. Accordingly, the collar device may monitor the number of avoidance events encountered. If a limit is exceeded, then . . .

the collar device may communicate with and activate toys to encourage wearer of the collar device to engage in alternative activities.

the collar device may trigger treat dispensers to dispense treats as a distraction.

Use Case Example

The collar device receives, monitors and collects avoidance/interaction data, collar device sensor data (including physiological condition data and activity level data), and/or environmental sensor data. Accordingly, the collar device may monitor a subset of physiological conditions and physical activity levels to determine if medicine should be introduced. If so, the collar device may cause an automatic dispenser to release medication.

Use Case Example

The collar device receives, monitors and collects avoidance/interaction data, collar device sensor data (including physiological condition data and activity level data), and/or environmental sensor data. Accordingly, a collar device may process data from a water bowl sensor indicating the water bowl level. If the level indicates low levels, then the collar device may communicate with and command a valve to open within the water bowl to refill (i.e. increase) the water level.

Use Case Example

The collar device receives, monitors and collects avoidance/interaction data, collar device sensor data (including physiological condition data and activity level data), and/or environmental sensor data. Accordingly, a collar device may receive/process data from a food dispenser sensor indicating that the food dispenser is in a jammed state. The collar may then report the condition to at least one application running on a remote server, i.e. the cloud computing platform. In turn the cloud computing platform may use general internet connectivity to forward alerts regarding the condition to a smartphone application. The cloud computing platform may provide such alerts via text message, email, or smartphone application interface. In such manner, a user may remotely monitor the status of the food dispenser.

Use Case Example

The collar device receives, monitors and collects avoidance/interaction data, collar device sensor data (including physiological condition data and activity level data), and/or environmental sensor data. Accordingly, a collar device may process data from a body weight scale. If the weight is above or below an ideal value, then . . .

the collar device may communicate with and activate toy (i.e., activity) devices within the premises to encourage activity while also monitoring subject response using collar device activity monitor;

the collar device may interact with food dispenser to limit the amount of food dispensed via a feeder if the measured weight is too high; alternatively the collar device may interact with food dispenser to provide excessive food amounts if the measured weight is too low;

the collar device may interact with a food weight scale to monitor the actual amount of food consumed;

the collar device may monitor subject response to the environmental changes via the physiological sensors within the collar.

Use Case Example

The collar device receives, monitors and collects avoidance/interaction data, collar device sensor data (including physiological condition data and activity level data), and/or environmental sensor data. Accordingly, the collar device may process data from a noise monitor sensor within the premises. If the noise level is over a prescribed limit, then . . .

the collar device may communicate with and activate toys to provide a distraction;

the collar device may communicate with and activate a treat dispenser to provide a distraction;

the collar device may communicate with and activate an Active Noise Cancellation system to minimize noise level.

Use Case Example

The collar device receives, monitors and collects avoidance/interaction data, collar device sensor data (including physiological condition data and activity level data), and/or environmental sensor data. Accordingly, the collar device may monitor and process data from co-located biological sensors indicating health status. Such sensors may be external to the subject and may monitor biological features of a subject from a distance. The collar may then report the monitored features to at least one application running on a remote server, i.e. the cloud computing platform. In turn the cloud computing platform may use general internet connectivity to forward alerts regarding such features to a smartphone application. The cloud computing platform may provide such alerts via text message, email, or smartphone application interface.

It should be noted that in the Use Case Examples provided above, the collar device analyzes avoidance/interaction data, collar device sensor data, and environmental sensor data to identify conditions and needs within the monitored premises. The collar device may then communicate with and command activity devices to perform certain functions to address such need or condition. In each Use Case Example, the collar device may then report the conditions, needs, and actions to at least one application running on a remote server, i.e. the cloud computing platform. In turn the cloud computing platform may use general internet connectivity to forward conditions, needs, and actions in the form of alerts or notifications to a smartphone application. The cloud computing platform may provide such alerts or notifications via text message, email, or smartphone application interface. In such manner, a user may remotely monitor the status of a monitoring/tracking/detecting system in real time.

It should be noted that in the Use Case Examples above, the collar device collects and analyzes avoidance/interaction data, collar device sensor data (including physiological conditions of a subject wearing the collar), and environmental sensor data in order to determine needs. The collar device then interacts with action/activity devices to address the need. However, the collar device may simply collect and forward such critical data to a remote application running on a remote computing platform which may then analyze the data to determine a particular need of a subject wearing the collar device. Once a need is determined, the remote application may determine and direct functional changes of activity devices within a premises of a monitoring/tracking/detecting system. The remote application may communicate with a collar device which then transmits function change information to activity devices to trigger actions designed to address the identified need. Further (and as already described above), the smartphone application may itself analyze collar device, environmental, and/or avoidance interaction data to diagnose needs and may itself direct function changes within the premises.

It should be noted that in the disclosure and examples provided above, activity devices generally control operation and performance of certain other devices with the monitored premises. However, such activity devices may themselves function as environmental sensors in the embodiments described above.

The wireless network of FIG. 12 may comprise a Wireless Personal Area Network (WPAN). A wireless personal area network (WPAN) is a personal area network for interconnecting devices usually centered within an individual person's living space or workspace. A wireless PAN is based on the standard IEEE 802.15. One type of wireless technology used for a WPAN includes the Bluetooth low energy (BLE) standard for personal area networks. Bluetooth low energy communication uses short-range radio waves to connect devices such as keyboards, pointing devices, audio headsets, printers, laptops, computers, embedded microcontrollers, personal digital assistants (PDAs), smart phones, tables, routers, sensor devices, monitoring devices, smart televisions, and streaming devices. Alternatively, a WPAN may also enable communications among networked components using Wireless USB, Zigbee or Z-Wave communication protocols. WPANs can be used for communication among the personal devices themselves (intrapersonal communication), or for connecting to a higher level network and the Internet (an uplink).

Figure 13:
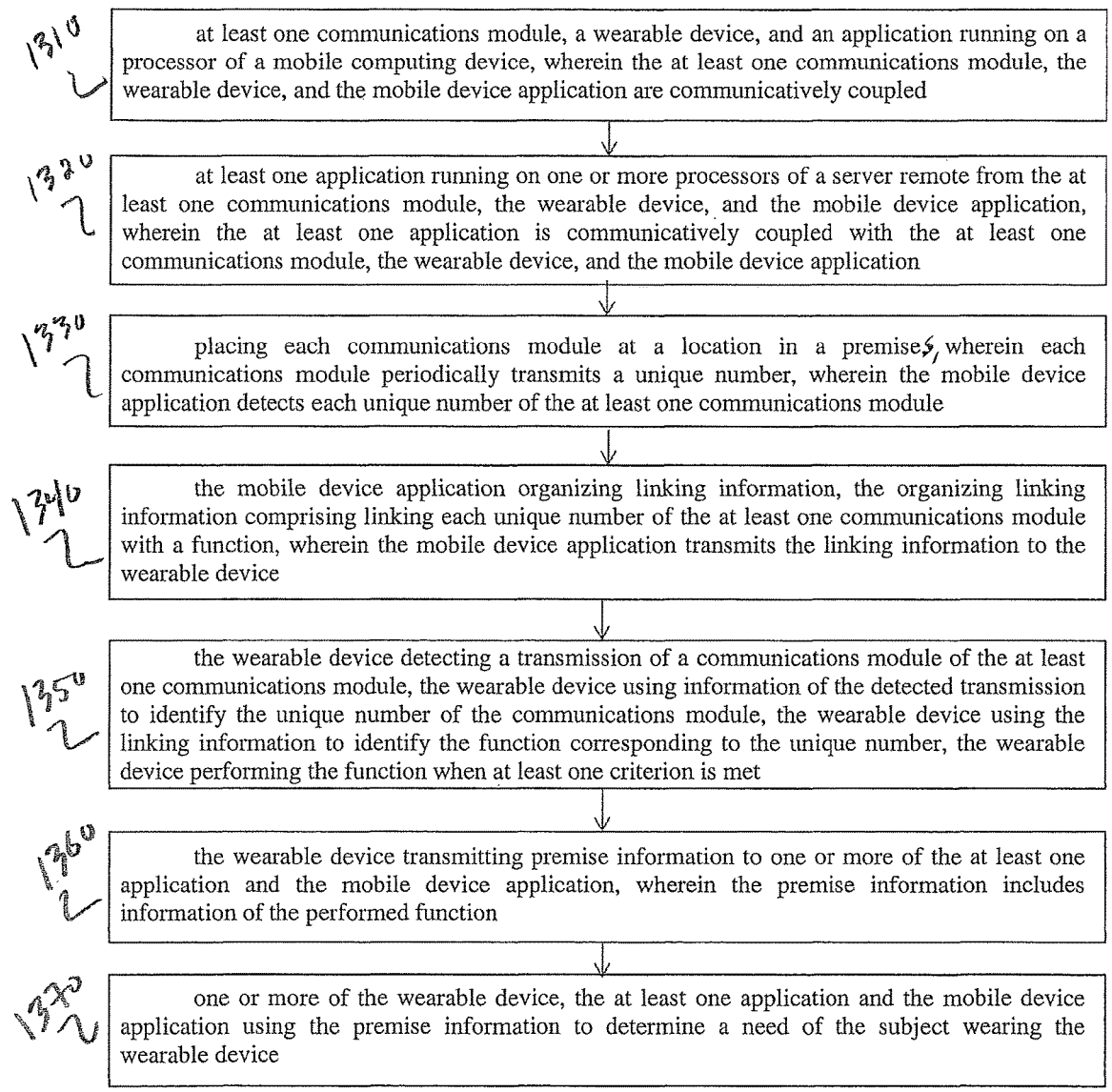
FIG. 13 shows a system for monitoring a subject in a premises, under an embodiment.

FIG. 13 shows a system for monitoring a subject in a premises. The system includes 1310 at least one communications module, a wearable device, and an application running on a processor of a mobile computing device, wherein the at least one communications module, the wearable device, and the mobile device application are communicatively coupled. The system includes 1320 at least one application running on one or more processors of a server remote from the at least one communications module, the wearable device, and the mobile device application, wherein the at least one application is communicatively coupled with the at least one communications module, the wearable device, and the mobile device application. The system includes 1330 placing each communications module at a location in a premises, wherein each communications module periodically transmits a unique number, wherein the mobile device application detects each unique number of the at least one communications module. The system includes 1340 the mobile device application organizing linking information, the organizing linking information comprising linking each unique number of the at least one communications module with a function, wherein the mobile device application transmits the linking information to the wearable device. The system includes 1350 the wearable device detecting a transmission of a communications module of the at least one communications module, the wearable device using information of the detected transmission to identify the unique number of the communications module, the wearable device using the linking information to identify the function corresponding to the unique number, the wearable device performing the function when at least one criterion is met. The system includes 1360 the wearable device transmitting premises information to one or more of the at least one application and the mobile device application, wherein the premises information includes information of the performed function. The system includes 1370 one or more of the wearable device, the at least one application and the mobile device application using the premises information to determine a need of the subject wearing the wearable device.

Figure 14:
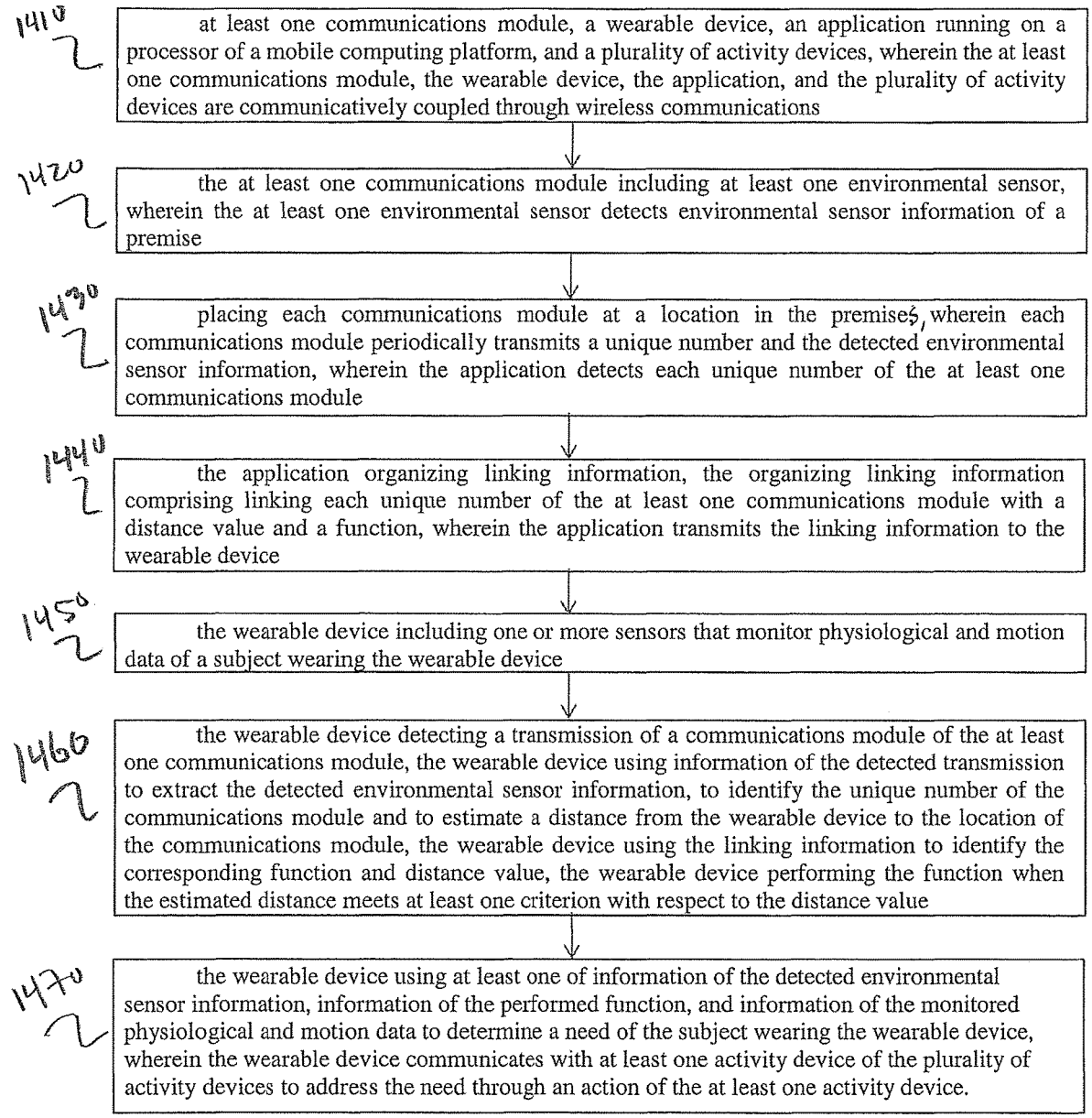
FIG. 14 shows a system for monitoring a subject in a premises, under an embodiment.

FIG. 14 shows a system for monitoring a subject in a premises. The system includes 1410 at least one communications module, a wearable device, an application running on a processor of a mobile computing platform, and a plurality of activity devices, wherein the at least one communications module, the wearable device, the application, and the plurality of activity devices are communicatively coupled through wireless communications. The system includes 1420 the at least one communications module including at least one environmental sensor, wherein the at least one environmental sensor detects environmental sensor information of a premises. The system includes 1430 placing each communications module at a location in the premises, wherein each communications module periodically transmits a unique number and the detected environmental sensor information, wherein the application detects each unique number of the at least one communications module. The system includes 1440 the application organizing linking information, the organizing linking information comprising linking each unique number of the at least one communications module with a distance value and a function, wherein the application transmits the linking information to the wearable device. The system includes 1450 the wearable device including one or more sensors that monitor physiological and motion data of a subject wearing the wearable device. The system includes 1460 the wearable device detecting a transmission of a communications module of the at least one communications module, the wearable device using information of the detected transmission to extract the detected environmental sensor information, to identify the unique number of the communications module and to estimate a distance from the wearable device to the location of the communications module, the wearable device using the linking information to identify the corresponding function and distance value, the wearable device performing the function when the estimated distance meets at least one criterion with respect to the distance value. The system includes 1470 the wearable device using at least one of information of the detected environmental sensor information, information of the performed function, and information of the monitored physiological and motion data to determine a need of the subject wearing the wearable device, wherein the wearable device communicates with at least one activity device of the plurality of activity devices to address the need through an action of the at least one activity device.

The components of a monitoring/tracking/detection system are described above. Under an embodiment of such system, a beacon located in a home environment periodically transmits data. A Bluetooth enabled receiver, i.e. an RF receiver, may roam within the environment and detect the data when the receiver is in close proximity to the beacon. The data comprises a beacon identification number. The receiver may then perform an action through use of a lookup table to associate a particular beacon identification number with a function. Under an alternative embodiment, the receiver may simply perform a function encoded in the transmitted data itself. In either case, RF beaconing enables the wireless exchange of information.

RF beaconing comprises a method of transferring data from one RF device to another. Under an embodiment the beaconed data is intended for RF receivers in close proximity to the RF beacon transmitter. An example of this is the iBeacon protocol standardized by Apple. This technology enables smartphones, tablets, and other devices to perform actions when in close proximity to an iBeacon. Under one embodiment, a shopper may walk down an aisle of a grocery store with smartphone in hand. A Bluetooth Low Energy (BLE) receiver in the shopper's phone may pick up iBeacon data being transmitted from store shelves announcing specials on nearby items. The receiver typically monitors its "Received Signal Strength Indicator" (RSSI) to indicate an approximate distance from the beacon which itself positioned near a particular item. If the receiver determines that the shopper is within a certain threshold distance from a particular item, the smartphone may report detected information regarding the item to a user through one or more smartphone applications. The shopper can then scan the nearby shelves for the specific item announced in the special.

The RF receiver may need to know without the intervention of human intelligence the actual range to a beacon, or even discriminate between two nearby beacon transmissions that are received simultaneously. Systems and methods for discriminating between two nearby beacon transmissions that are received simultaneously are described below.

Typically, the actual range from a receiver to a transmitter may be estimated based on the RSSI values on the receive side. The problem is that this value can vary greatly based on antenna orientation, environment, obstructions, receiver proximity to a body, and many other factors. It is possible to mitigate the variances by averaging RSSI values across multiple beacon transmissions. This method serves to reduce, but not eliminate the variances. A functional system takes these RSSI variances into account when determining an expected activation range. For example, it must be understood that an RSSI value may represent a distance of anywhere from 1 meter to 3 meters depending on orientation of a beacon transmitter with respect to a nearby body and position of the RF receiver on the body itself.

This method is acceptable in some use cases, but not all. For example, it may be required that a system only activate upon very close proximity to a beacon; alternatively, it may required that a system determine whether it is very close to a first beacon device when another beacon device is in close proximity. In other words, the first beacon may serve as a location proxy for a first location and the second beacon may serve as a location proxy for a second location. In receiving transmissions from both beacons simultaneously, simple RSSI distance estimation may generate false positive detection events, i.e. false detection of an "at" proximity with respect to one or both locations.

A pet monitoring system provides an example of the problem under one embodiment. In operation of the system, assume that a dog collar includes a Bluetooth Low Energy (BLE) receiver. Further assume that various products distributed throughout the monitored environment are outfitted with BLE beacons. Each beacon broadcasts data about a corresponding device. Examples of beacon-enabled devices may include under one embodiment:

a pet food bowl that broadcasts the following: function (food bowl; log pet proximity), battery level, and transmit power (to help the receiver calibrate RSSI from different power level beacons);

a pet water bowl that broadcasts the following: function (water bowl; log pet proximity) and transmit power (to help the receiver calibrate RSSI from different power level beacons);

a beacon buried under a couch cushion that broadcasts the following: function (avoidance; correct pet if it gets too close), battery level, and transmit power (to help the receiver calibrate RSSI from different power level beacons).

Some applications of the pet monitoring system only require crude RSSI resolution. As one example, a pet roams the monitored environment of the pet monitoring system and approaches an avoidance beacon buried under the couch cushion. The BLE-enabled pet collar, i.e. receiver, monitors under an embodiment beacon transmissions and associated RSSI levels. When the RSSI level surpasses a designated threshold, a determination is made that the pet has entered a region where a correction is to be applied to encourage the pet to back away. This region does not have to be an exact distance, as long as it is sufficient enough to keep the pet off of the couch cushion.

As the pet, i.e. the BLE enabled pet collar of the pet monitoring system, continues to roam the monitored environment, it may approach an area where a beacon-enabled water bowl and beacon-enabled food bowl reside. Under one embodiment, a pet collar logs duration of proximity to the water bowl, periods of time when the pet wearing the collar is drinking water from a water bowl (i.e. in very close proximity), and duration of proximity to a food bowl, periods of time when the pet wearing the collar is eating from the food bowl (i.e. in very close proximity). This is a very difficult task to perform utilizing RSSI signal levels as the standard of error inherent to RSSI distance estimation blurs the distinction between "near the bowl" and "at the bowl". If both the water bowl and food bowl are in close proximity to each other, the collar receiver may detect both signals in a closely overlapping region making discrimination between the signal sources impossible. Under an embodiment, the receiver may know that a first transmission is from the food bowl because the transmission includes identification data. Likewise the receiver may know that a second transmission is from the water bowl because the transmission includes identification data. But the receiver cannot discriminate just how close it is to either one meaning that the receiver cannot determine that it is very close to one object but not the other.

RSSI is commonly used for proximity determination between a receiver and advertising beacon. However, RSSI estimations may be affected by positioning, obstructions, environment, and many other factors. Variance in detected RSSI levels may lead to one or more of the following:

over-sampling and averaging of multiple readings over time which then extends proximity determination time;

allowing large tolerances in proximity determination, i.e. allowing a wide range of RSSI values to map onto a discrete distance estimate;

failure to discriminate between nearby objects outfitted with beacons due to similarity of RSSI values simultaneously detected from collocated beacons.

Under one embodiment the typical, imprecise Received Signal Strength Indicator (RSSI) based proximity determination capability of an RF receiver may be augmented with range-determination technologies. Such technologies may be located within the circuitry of the broadcasting beacons. The range-determination technologies detect environmental data within a range of the beacon. The RF beacon may include information of these data, i.e. conditions, distance determinations, time determinations, occurrences, and environmental phenomena, in the RF beacon's data transmission. The RF receiver may use this information to more precisely calculate the range between the beacon and RF receiver.

Examples of range-determination technologies include under one embodiment one or more of the following:

Capacitive sensor: detecting the presence of an object that is conductive or has a dielectric different from air including human and animal bodies.

Inductive sensor: detecting the presence of a metallic object.

Infrared ranging: a first type detecting the presence of an object within a specified range from the transmitter.

Infrared Ranging: a second type measuring the range of an object from the transmitter using two-way ranging.

Passive Infrared (PIR) sensor: detecting an object in motion within the field of view.

Ultrasonic Ranging: measuring the range of an object from the transmitter.

Laser: precisely measuring the range of an object from the transmitter.

Magnetic sensor: detecting the presence of a magnetic object.

The RSSI proximity estimate proceeds under one embodiment as follows:

An RF beacon transmits a data packet on a schedule (i.e. once per second; once per 200 mS; etc.)

An RF receiver detects transmissions of a beacon.

An RF receiver decodes the transmissions.

An RF receiver calculates an RSSI of the RF Beacon transmission. Note that for applications requiring greater accuracy, RSSI values corresponding to multiple packets from the beacon of interest are averaged together.

An RF receiver determines an estimated range between the RF Receiver and RF Beacon based on the calculated RSSI result.

The range determination based on this calculated RSSI value may be imprecise as such values are significantly affected by positioning, obstructions and environment. If the range and/or beacon discrimination based on the RSSI reading(s) is acceptable for an application, the process is complete, and the RF receiver performs an action if a ranging threshold is surpassed.

If the distance estimation and/or beacon discrimination based on the RSSI readings is not acceptable for a given application, the RF Beacon circuitry may be enhanced with the addition of one or more presence/ranging technologies capable of detecting the presence and/or range of nearby objects. The RF Beacon may include the results of the detected presence/ranging data in the RF Beacon transmission. The RF Receiver may analyze its range relative to the RF Beacon utilizing both the initial RSSI distance determination and the presence/ranging data included in the RF Beacon transmission. If the enhanced range determination meets the ranging threshold of an RF Receiver application, then the RF Receiver may perform its prescribed action.

Figure 15:
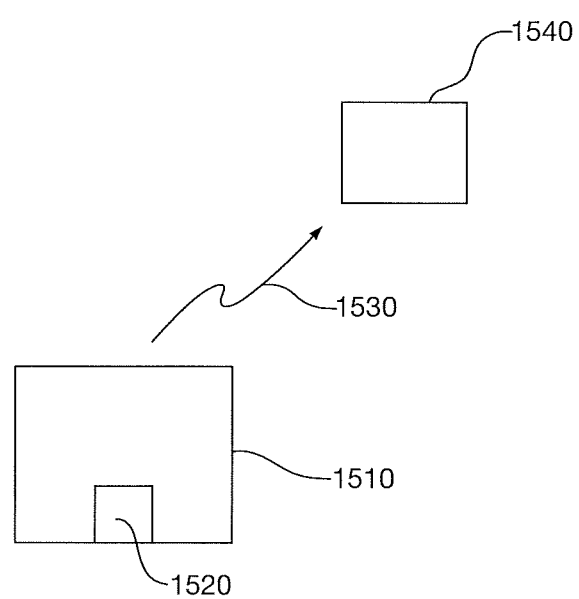
FIG. 15 shows an RF Beacon sending repetitive transmissions, under an embodiment.

FIG. 15 shows an RF Beacon 1510 sending repetitive transmissions 1530. The RF Beacon includes a presence/technology 1520. Such technology may comprise a capacitive sensor, inductive sensor, infrared ranging detector, passive infrared (PIR sensor), ultrasonic ranging, laser, and/or a magnetic sensor. An RF Receiver 1540 detects the repetitive transmissions of the beacon. RF Beacon and RF Receiver communicate under one embodiment using a Bluetooth Low Energy standard.

Figure 16:
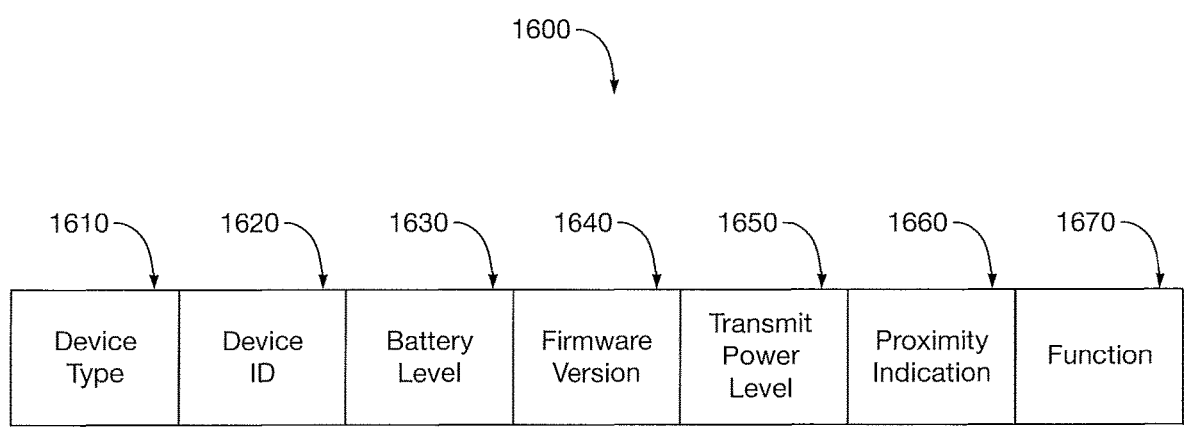
FIG. 16 shows the content of an RF Beacon data packet, under an embodiment.

FIG. 16 shows the content of an RF Beacon data packet 1600. The data packet includes device type 1610, device id 1620, battery level 1630, firmware version 1640, transmit power level 1650, proximity indication 1660, and function 1670. Proximity indication comprises data corresponding to the presence/ranging technologies. For example, if a capacitive sensor detects a close proximity of a pet body, then the corresponding RF Beacon transmits data of the event, i.e. proximity indication, as a component of its repetitive communications.

Figure 17:
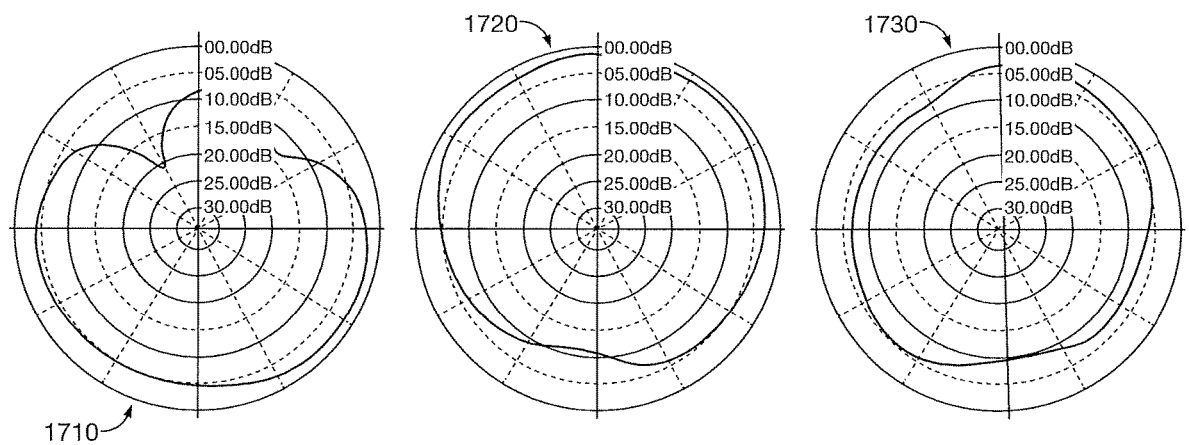
FIG. 17 shows example antennae patterns demonstrating differing signal strength levels depending on the approach angle of an RF Receiver relative to the respective RF Beacon, under an embodiment.

FIG. 17 shows example antennae patterns 1710, 1720, 1730 demonstrating differing signal strength levels depending on the approach angle of an RF Receiver relative to the respective RF Beacon.

Figure 18:
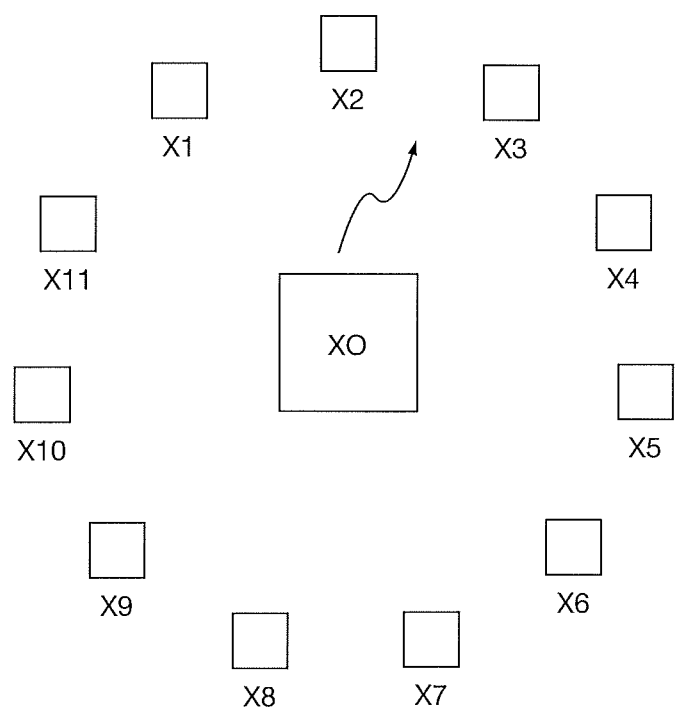
FIG. 18 shows a transmitting RF Beacon in proximity to various RF Beacons, under an embodiment.

FIG. 18 shows a transmitting RF Beacon X0. FIG. 18 also shows RF Receivers X1-X11 positioned at various locations around the RF Beacon, i.e. positioned at differing approach angles. The RF Receivers detect the following signal strength (RSSI) levels.

| | |
|---|---|
| X1 | −67 dB |
| X2 | −71 dB |
| X3 | −72 dB |
| X4 | −66 dB |
| X5 | −70 dB |
| X6 | −70 dB |
| X7 | −66 dB |
| X8 | −73 dB |
| X9 | −71 dB |
| X10 | −70 dB |
| X11 | −68 dB |

Figure 19:
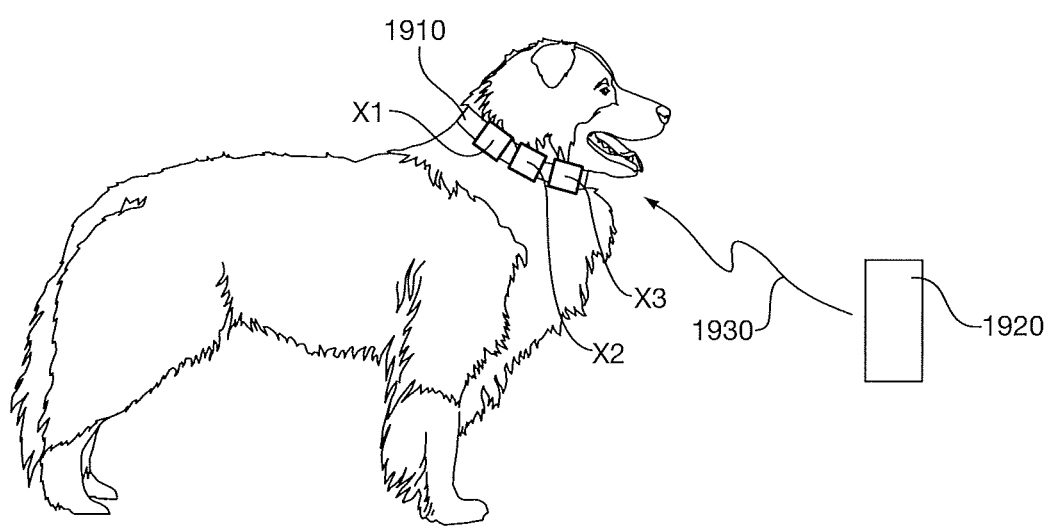
FIG. 19 shows a dog with a collar comprising an RF Receiver in an environment that includes an RF Beacon, under an embodiment.

FIG. 19 shows a dog with a collar 1910 that includes an RF Receiver. The RF Receiver of course repositions itself relative to the pet body over time as the pet and collar move around within an environment. FIG. 19 also shows an RF Beacon 1920 periodically transmitting 1930 RF Beacon data. The various RF receiver collar positions (X1-X3, shown; X4-X6, not shown) register the following RSSI signal strength levels:

| | |
|---|---|
| X1 | −67 dB |
| X2 | −70 dB |
| X3 | −65 dB |
| X4 | −72 dB |
| X5 | −71 dB |
| X6 | −66 dB |

Under one embodiment of a pet monitoring system, a pet collar includes an RF Receiver. The receiver communicates with an RF Beacon incorporated into or affixed to a water bowl. The receiver logs close-proximity interactions between a pet wearing the collar and the beacon equipped water bowl.

Once a specified RSSI threshold value is surpassed, the RF Receiver knows that it is close to the water bowl; however, the RSSI distance estimate is not precise enough to establish with confidence that the pet is close enough to be drinking water versus just "nearby" the water bowl. Imprecision in the estimate may be due to one or more of an approach angle of the pet to the water bowl, position of the RF Receiver on the pet's neck, and the position of the RF Beacon on the water bowl. However, it is imperative that the log entry only occur upon very close proximity.

In order to increase the precision of the RSSI proximity estimate, a capacitive sensor is under one embodiment added to the circuitry of the RF Beacon. Upon very close approach of the pet body to the water bowl, the capacitive sensor begins to react. The reaction (sensor data) may be included in the data packet sent out by the RF Beacon. Once the RSSI threshold has been surpassed, AND the sensor data packet from the RF Beacon includes confirmation that a pet body is very nearby, the RF Receiver may confidently log the interaction.

Figure 20:
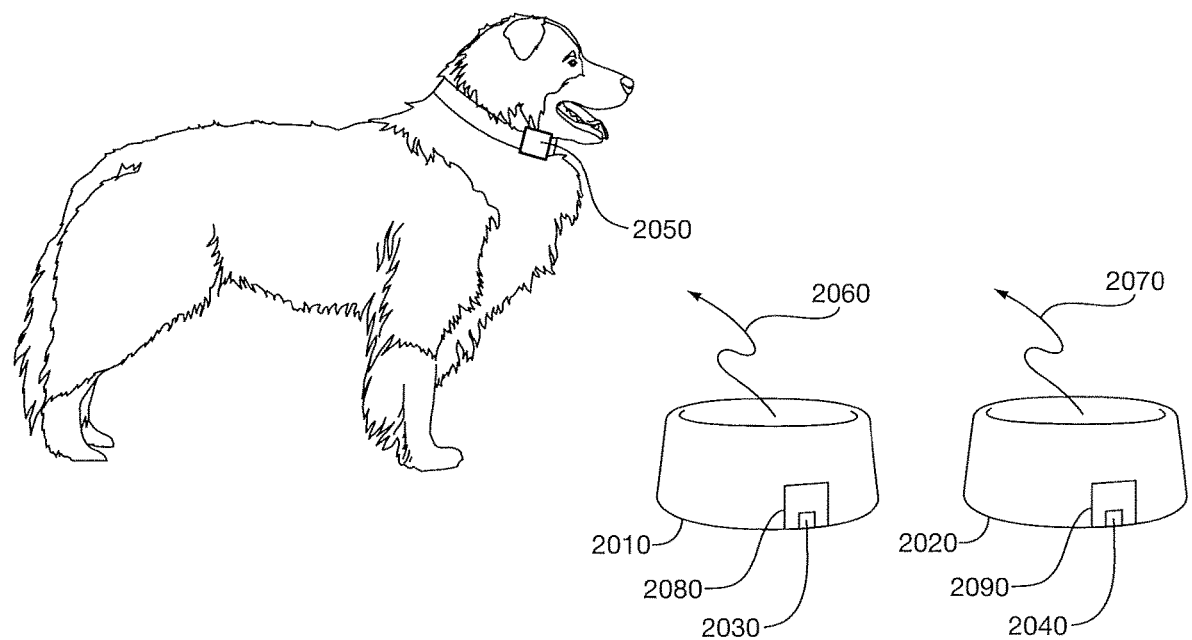
FIG. 20 shows a dog with a collar comprising an RF Receiver in an environment that includes two RF Beacons, under an embodiment.

With reference to FIG. 20, assume that an RF Receiver roams in proximity to two RF Beacon equipped bowls—a food bowl 2010 and a water bowl 2020. The food bowl 2010 features beacon 2080. Water bowl 2020 features beacon 2090. Each bowl also comprises a capacitive sensor 2030, 2040 for detecting near proximity of the pet wearing the RF Receiver. As the pet approaches the bowls, RF Receiver 2050 detects similar RSSI levels from the first RF Beacon 2060 and the second RF Beacon 2070. These RSSI levels surpass a threshold to indicate close proximity. However, the first capacitive sensor 2030 detects near proximity of the pet body while the second first capacitive sensor 2040 does not. This means that the first RF Beacon transmission 2060 contains capacitive sensor data indicating proximity while the second RF Beacon transmission 2070 does not. Despite reading identical RSSI levels from both RF Beacons, the RF receiver is now aware of close proximity to the food bowl but not the water bowl.

Assume that an RF Receiver approaches an RF Beacon equipped trash can. Depending on the position of the RF Receiver on the pet's neck, the approach angle of the pet to the trash can, and the position of the RF Beacon on the trash can, the RSSI value can vary significantly. Once a specified RSSI threshold value is surpassed, the RF Receiver knows that it is close to the trash can, however, not precisely enough to confidently apply a stimulus to the pet to discourage interaction between the pet and trash can.

Figure 21:
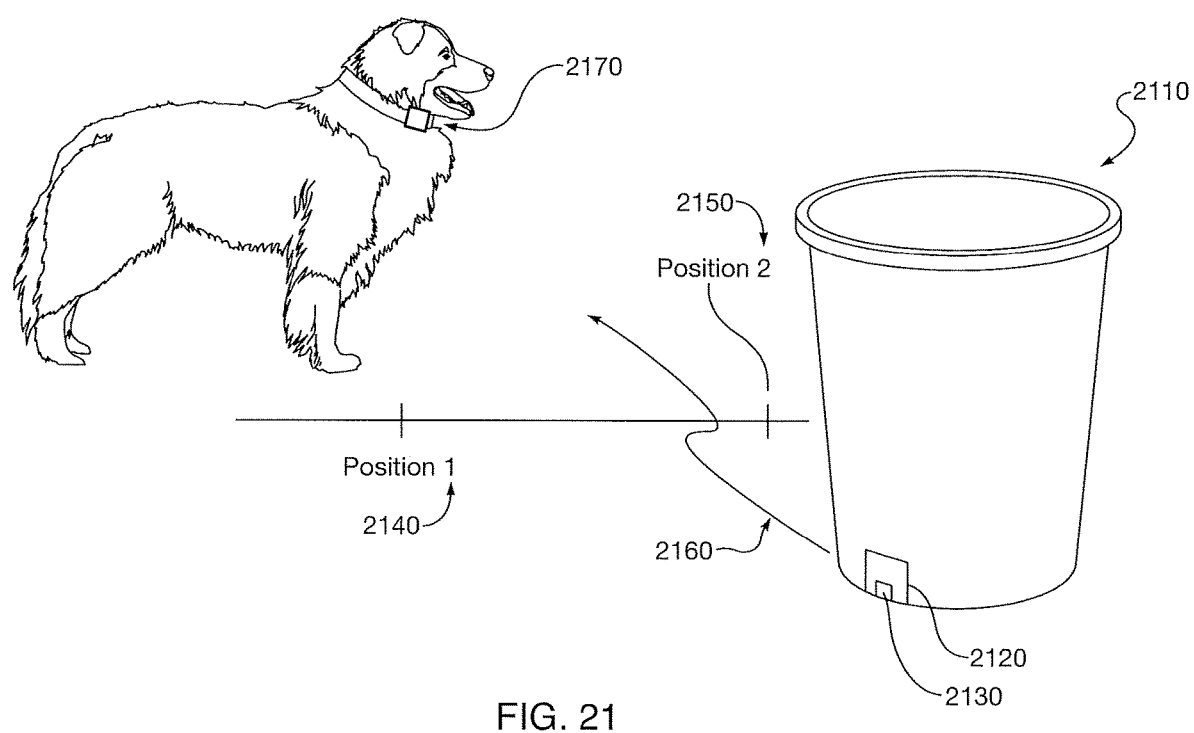
FIG. 21 shows a dog with a collar comprising an RF Receiver in an environment that includes an RF Beacon, under an embodiment.

With reference to FIG. 21, trash can 2110 is equipped with an RF Beacon 2120 which itself includes a capacitive sensor 2130. As the pet wearing the RF Receiver 2170 approaches the trash can, the receiver passes through a first position 2140 on its way to a second position 2150 in close proximity to the trash can 2110. However, possibly due to a change in the pet's position, the RF receiver 2170 detects similar RF readings at both positions. However at the second position the capacitive sensor 2130 senses close proximity of the pet body. When the pet is at the second position, the RF Beacon transmissions 2160 include capacitive sensor data indicating close proximity. The combination of RSSI level and confirmed capacitive sensor event causes a pet collar to apply a stimulus encouraging the pet to exit an avoidance area surrounding the trash can.

Under one embodiment, RF Receiver/Beacon components interact to provide a product coupon when an in store shopping consumer is directly in front of the product for a given period of time. Under this embodiment, the consumer uses a smartphone that supports RF Receiver capability (likely Bluetooth Low Energy) while the store shelf itself comprises an RF Beacon positioned near the product of interest.

Figure 22:
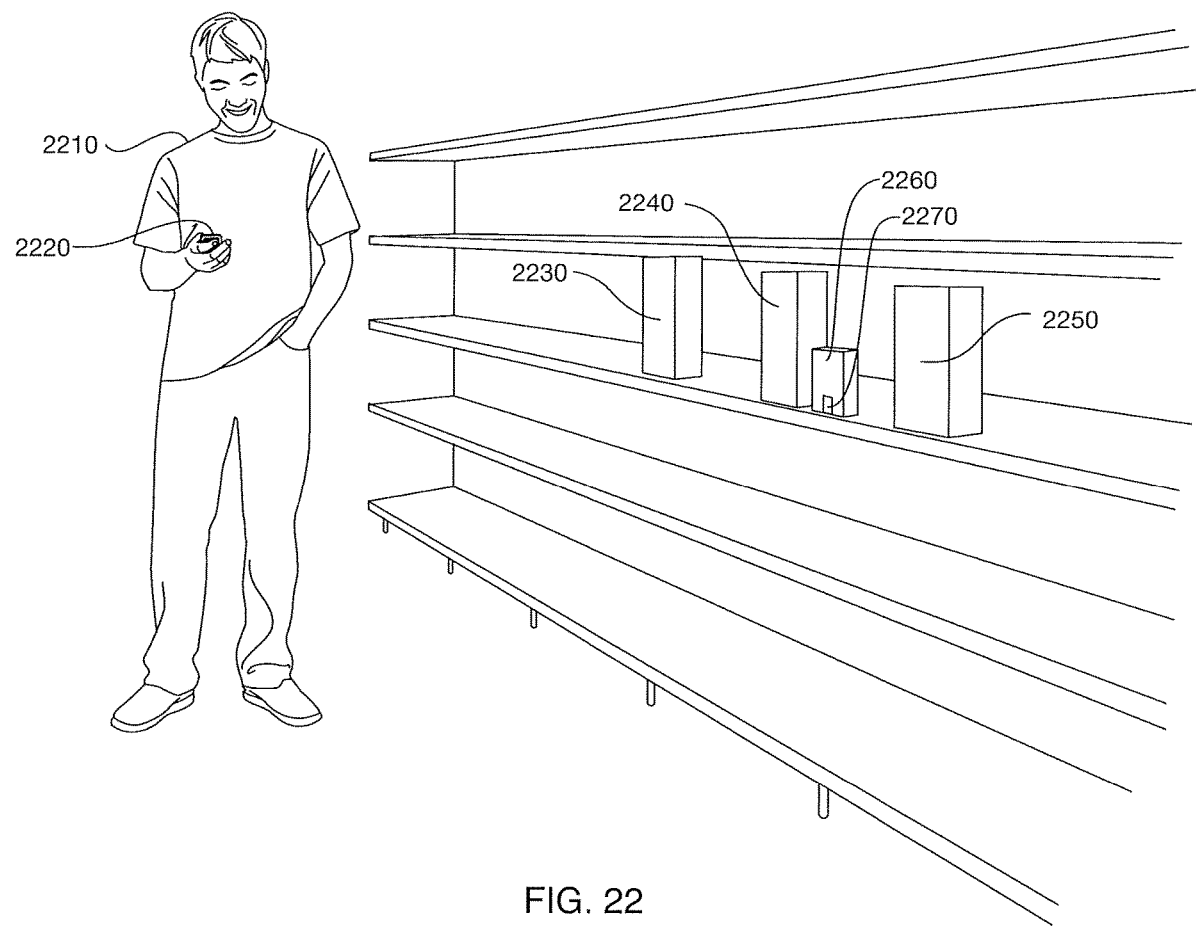
FIG. 22 shows a consumer operated smartphone comprising an RF Receiver in an environment that includes an RF Beacon, under an embodiment.

With reference to FIG. 22 a consumer 2210 with smartphone 2220 approaches a product shelf to inspect an array of products. The shelf displays a first product 2230, a second product 2240, and a third product 2250. An RF Beacon 2260 may be placed directly behind, underneath or above the second product. Once a specified RSSI threshold value is surpassed, the RF Receiver within the consumer's cell phone knows that it is close to an advertising beacon. However, the smartphone RF receiver may detect similar RSSI levels when in front of any of the three products. The smartphone RF receiver does not detect RSSI levels precisely enough to confidently know that the consumer is directly in front of the product that is coupon-enabled by an RF Beacon. It is imperative that the notification of the consumer occur only when the consumer is directly in front of the product for a specified period of time indicating the consumer has an interest in the product.

Under an embodiment, the RF Beacon of an embodiment includes an ultrasonic ranging sensor 2270. Upon approach of the consumer to the RF Beacon, within the tight field-of-view of the ultrasonic ranging sensor, the ultrasonic ranging sensor 2270 calculates the precise distance between the ultrasonic ranging sensor and consumer and includes this value within the data packet of the advertising RF Beacon. Once the RSSI threshold has been surpassed, and the data packet from the RF Beacon includes the further confirmation that the consumer has been stationary within close range for a sufficient time, an electronic coupon may be sent to the consumer's smartphone.

Figure 23:
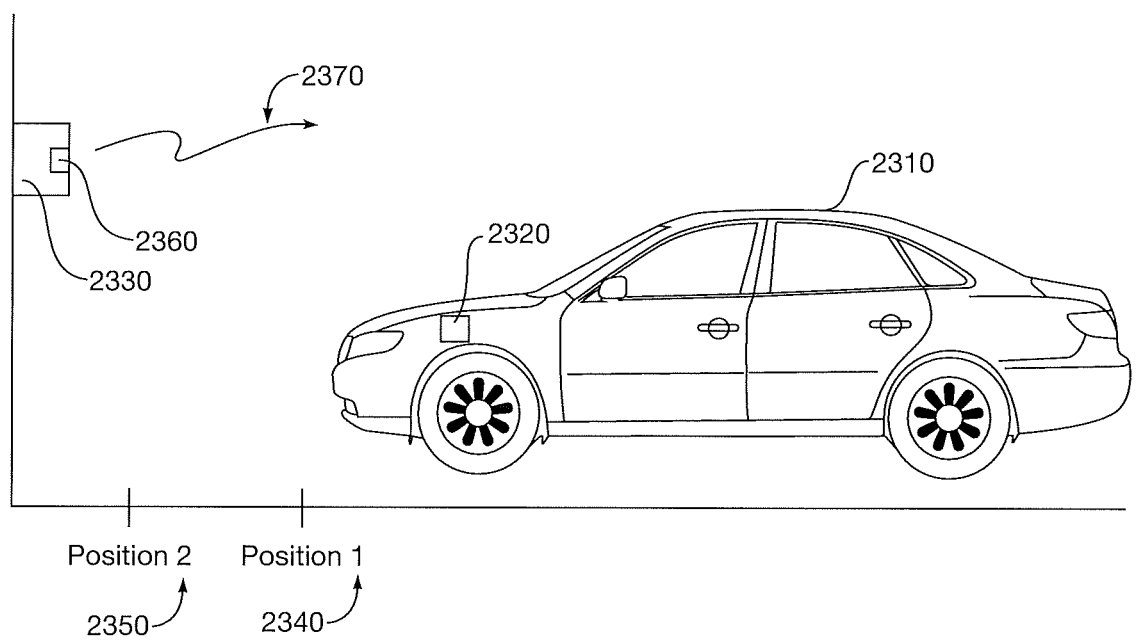
FIG. 23 shows a vehicle comprising an RF Receiver in an environment that includes an RF Beacon, under an embodiment.

Under one embodiment, RF Receiver/Beacon components interact to provide a driver vehicle position information relative to an interior wall of a garage. With reference to FIG. 23, a driver moves a vehicle 2310 forward to position it within a garage space. The vehicle includes an RF Receiver 2320 located in a forward position while the interior wall of the garage includes an RF Beacon 2330. In approaching the interior wall, the vehicle moves from a first position 2340 to a second position 2350. In the first position a closing garage door will strike the back end of the vehicle. In the second position the front end of the car is sufficiently near to the interior wall (without risk of any collision between vehicle and wall) to provide clearance between the back end of the vehicle and a closed garage door.

However, the RF Receiver detects similar RSSI levels at the first position and the second position. The vehicle RF receiver does not detect RSSI levels precisely enough to confidently establish the vehicle's position within the garage space. It is imperative that the vehicle pull up a fairly precise point to avoid contact with the wall and to allow the garage door to close behind the car.

Under an embodiment, the RF Beacon may include an inductive sensor 2360 within its circuitry. The inductive sensor may detect nearby metal. Upon approach of the metallic vehicle toward the interior garage wall, the inductive sensor 2360 begin to reacts. The reaction data may be included in the data packets transmitted 2370 by the RF Beacon. Once an RSSI level threshold has been surpassed and the corresponding data packets from the RF Beacon include further confirmation of an inductive sensor event, i.e. that the vehicle is within a range of the inductive sensor, the RF receiver may notify the driver that the vehicle is in a proper location. The RF Receiver may cooperate with sound emitting devices to provide the notification. Alternatively, the RF Receiver may cooperate with electronics within the vehicle to provide the notification via audible or visible alerts.

Figure 24:
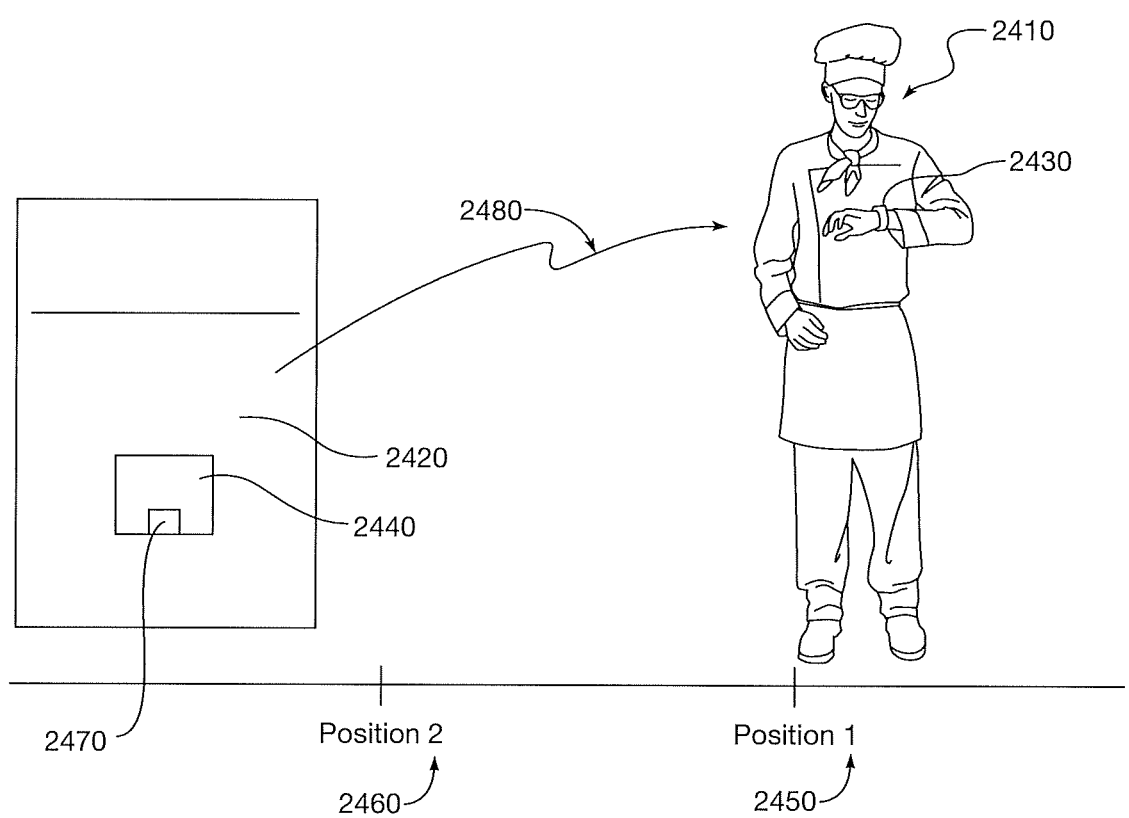
FIG. 24 shows a wristband comprising an RF Receiver worn by a cook in an environment that includes an RF Beacon, under an embodiment.

With reference to FIG. 24, a cook 2410 at a restaurant may work near a dangerously hot surface 2420. The cook may be outfitted with a wrist-mounted RF receiver 2430, while the hot surface 2420 may be outfitted with an RF beacon 2440. The cook may move from a first position 2450 to a second position 2460. The second position represents dangerous proximity to the hot surface.

Figure 25:
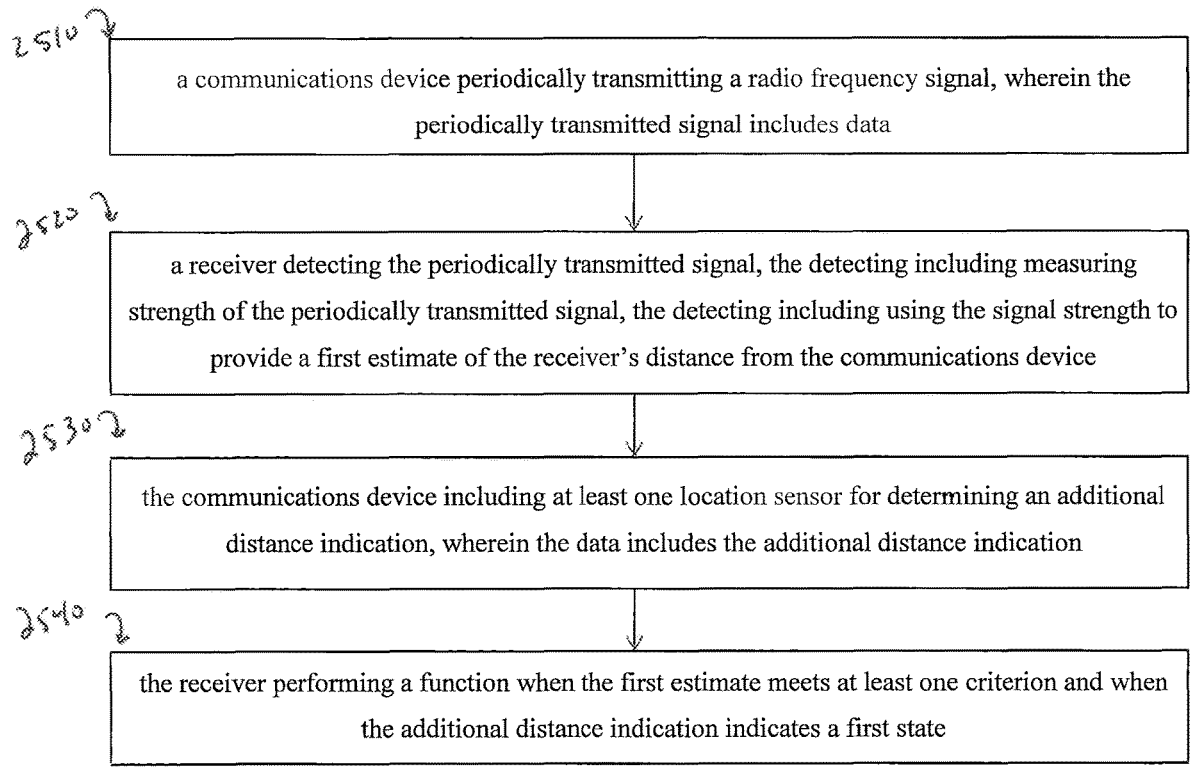
FIG. 25 shows a system for enhancing RF Beacon proximity determination, under an embodiment.

FIG. 25 shows a system for enhancing RF Beacon proximity determination. The system comprises 2510 a communications device periodically transmitting a radio frequency signal, wherein the periodically transmitted signal includes data. The system comprises 2520 a receiver detecting the periodically transmitted signal, the detecting including measuring strength of the periodically transmitted signal, the detecting including using the signal strength to provide a first estimate of the receiver's distance from the communications device. The system comprises 2530 the communications device including at least one location sensor for determining an additional distance indication, wherein the data includes the additional distance indication. The system comprises 2540 the receiver performing a function when the first estimate meets at least one criterion and when the additional distance indication indicates a first state.

However, the RF Receiver detects similar RSSI levels at the first position and the second position. The RF receiver does not detect RSSI levels precisely enough to confidently establish the cook's location with respect to the hot surface. Under an embodiment, the RF Beacon may include an infrared ranging sensor 2470 within its circuitry. Upon the cook's approach toward the dangerous region, the infrared ranging sensor 2470 will measure the distance from the hot surface to the cook and place the result in the data packet sent out by the RF Beacon. In other words, the infrared ranging sensor data may be included in the data packets transmitted 2480 by the RF Beacon. Once an RSSI level threshold has been surpassed and the corresponding data packets from the RF Beacon include further confirmation of an infrared ranging sensor event, i.e. confirmation that the cook is in the second position or rather within a dangerous range of the infrared ranging sensor, the RF Receiver may notify the cook of danger.

Use of Monitoring/Tracking/Detection System to Provide a Sound Masking Environment Systems and methods for monitoring a subject in a premises are described above in detail. Under the systems and methods described above, a monitoring/tracking/detection system includes one or more collar devices, one or more beacons, and at least one smartphone running an application and providing user interaction with such system. FIG. 2 shows one embodiment of a system for monitoring/tracking/detecting activities of a subject within a premises. FIG. 2 shows a mobile device 210 running a smartphone application. The smartphone application is communicatively coupled to collar devices 220, 230. The smartphone application may transmit data to and control certain functions of the collar devices 220, 230 as described above. The smartphone application may also receive data from collar devices as described above. FIG. 2 shows collar devices 220, 230 communicatively coupled to beacons 240, 250, 260. The collar devices receive data periodically transmitted by beacons 240, 250, 260 and otherwise communicate with beacons 240, 250, 260 as described above. The smartphone application 210 may assign certain functionality directly to beacons 240, 250, 260 and otherwise communicates with beacons as described above.

An additional embodiment of the monitoring/tracking/detection system may include additional sensors or devices that proactively monitor and manage the health and well being of a subject under observation within the protected/monitored premises. These additional sensors/devices include collar device sensors, environmental sensors, and action or activity sensors. A monitoring/tracking/detection system including the devices and sensors described above provide pro-active health and well being functionality under one embodiment. Such system may provide a sound masking environment under an embodiment.

A monitoring/tracking/detection system directed to a sound-masking embodiment is described below. Such system comprises under an embodiment a wearable sound-masking component created to deliver various noise types to mask other distracting noises such as; thunderstorms, passing vehicles, newspaper deliveries, fireworks, other pets, raccoons, birds, possums, wind, etc. Under an embodiment, the collar device of the monitoring/tracking/detection system includes the sound masking component as further described below.

Dogs can hear much higher frequencies than humans. The hearing of dogs can also be more than four times greater than their owners. Canines can tilt, rotate, raise, and lower their ears to hone in on sounds. They can even hear with each ear independently. This gifted sense of hearing may also be a source of barking, whining, anxiety, and worry due to increased stimulus levels. The small, normal, non-threatening noises of an animal's environment may cause a dog anxiety and induce barking events.

A wearable sound masking system includes an article wearable by a dog, i.e. a collar with a sound masking source/component. Note that under an alternative embodiment, a sound masking component may be located elsewhere on the animal. Under such embodiment the sound masking component is external to the collar and also communicatively coupled to the collar device. As another example, the sound masking dog component may be implemented as a small attachment for clipping on any collar when the need arises and easily removed as needed. (It should be noted that the sound masking component may simply be referred to below as a sound masking collar, sound masking collar device, sound masking dog collar, or sound masking dog collar device). The sound masking source operates by "covering up" or masking, "anxiety-causing" and "bark-inducing" sounds such as: thunderstorms, passing vehicles, newspaper deliveries, fireworks, other pets, raccoons, birds, possums, wind, etc. The focus is not on delivering music or tones to a dog's ears. Rather, the system of an embodiment is designed to accomplish quite the opposite. It is created to mask bark-provoking, or anxiety-inducing sounds from ever being detected. The sound masking dog collar is designed to humanely mask such causes of anxiety through the "Power-Spectrum of frequency signals". A familiar method of sound masking is the use of "white noise". The "color" of noise also includes brown noise, pink, red, blue, violet, grey, etc. The aforementioned colors are similar to white noise, but with more energy concentrated at various areas of the sound spectrum, which subtly changes the nature of the signal. Pink noise, for example, is like white noise with more energy concentrated at the lower end of the frequency spectrum. Sound waves have two fundamental characteristics: frequency, which is how fast the waveform is vibrating per second (one hertz is one vibration per second), and amplitude, which is the power or size of the waves. The noise types are named for a loose analogy to the colors of light: White noise, for example, contains all of the audible frequencies, just like white light contains all of the frequencies in the visible spectrum.

While "sound machines" or "white noise machines" may be helpful if placed near your pet, most dogs choose to move around their environment. They explore, drink water, eat food, and wander. But, by placing the sound masking dog collar on your dog, the masking remains constant for the animal as he moves around his home. The volume and noise type (i.e. white, pink, etc.) can be adjusted by the owner based on their individual dog's response. Alternatively, the noise variables can set automatically by the software based on the type of sound causing a problem for the pet. The distracting-sound-type may be set by the pet owner or automatically detected by connected sensors (as further described below).

The sound masking dog collar is designed under an embodiment to prevent a dog from hearing these distractions at all. It is meant to mask the detection of sound. It actually delivers a constant buzz that is meant to vibrate the eardrum in such a way that the dog does not detect distractions, anxiety causing sounds, or bark-provoking noises.

The mechanism of sound masking can be explained by analogy with light. In a dark room where someone is turning a lamp on and off, the light will be obviously noticeable. However, if the overhead lights are turned on, turning on the lamp may no longer be as distracting because it has been "masked". Sound masking operates by masking unwanted sounds, similar to perfume that covers up other odors. This is in contrast to attempts toward eliminating unwanted music or tones.

Similarly, certain noise types may reduce the effects of unwanted sounds by calming the pet. Pink noise has a calming effect on pets. Even if distracting noises are not totally masked by the sounds being generated by the collar (as further described below) the collar can keep a pet from having an adverse reaction to the unwanted sounds.

The masking sound emitted by the sound masking collar may comprise pink noise, under an embodiment. The frequency spectrum of pink noise is linear in logarithmic scale; it has equal power in bands that are proportionally wide. This means that pink noise would have equal power in the frequency range from 40 to 60 Hz as in the band from 4000 to 6000 Hz. Since humans hear in such a proportional space, where a doubling of frequency (an octave) is perceived the same regardless of actual frequency (40-60 Hz is heard as the same interval and distance as 4000-6000 Hz), every octave contains the same amount of energy and thus pink noise is often used as a reference signal in audio engineering. The spectral power density, compared with white noise, decreases by 3 dB per octave (density proportional to 1/f). For this reason, pink noise is often called "1/f noise".

The masking sound emitted by the sound masking collar may comprise white noise, under an embodiment. White noise is a signal (or process), named by analogy to white light, with a flat frequency spectrum when plotted as a linear function of frequency (e.g., in Hz). In other words, the signal has equal power in any band of a given bandwidth (power spectral density) when the bandwidth is measured in Hz. For example, with a white noise audio signal, the range of frequencies between 40 Hz and 60 Hz contains the same amount of sound power as the range between 400 Hz and 420 Hz, since both intervals are 20 Hz wide. Note that spectra are often plotted with a logarithmic frequency axis rather than a linear one, in which case equal physical widths on the printed or displayed plot do not all have the same bandwidth, with the same physical width covering more Hz at higher frequencies than at lower frequencies. In this case a white noise spectrum that is equally sampled in the logarithm of frequency (i.e., equally sampled on the X axis) will slope upwards at higher frequencies rather than being flat.

The masking sound emitted by the sound masking collar may comprise Brownian noise, under an embodiment. The terminology "red noise", also called Brown noise or Brownian noise usually refers to a power density which decreases 6 dB per octave with increasing frequency (density proportional to $1/f^2$) over a frequency range which does not include direct current (in a general sense, does not include a constant component, or value at zero frequency). In areas where terminology is used loosely, "red noise" may refer to any system where power density decreases with increasing frequency.

The masking sound emitted by the device may comprise blue noise, under an embodiment. Blue noise is also called azure noise. Blue noise's power density increases 3 dB per octave with increasing frequency (density proportional to f) over a finite frequency range.

The masking sound emitted by the sound masking collar may comprise violet noise, under an embodiment. Violet noise is also called purple noise. Violet noise's power density increases 6 dB per octave with increasing frequency (density proportional to $f^2$) over a finite frequency range. It is also known as differentiated white noise, due to its being the result of the differentiation of a white noise signal.

The masking sound emitted by the sound masking collar may comprise grey noise, under an embodiment. Grey noise is random white noise subjected to a psychoacoustic equal loudness curve (such as an inverted A-weighting curve) over a given range of frequencies, giving the listener the perception that it is equally loud at all frequencies.

In operation of a "proactive health and well-being" monitoring/tracking/detection system directed to a sound masking embodiment, a collar device collects a wealth of information as it roams throughout the monitored premises. First, the collar device may collect data with respect to avoidance/tracking events (otherwise referred to herein as avoidance/interaction events) triggered by proximity to particular beacons. (Note that avoidance/tracking events and the logging of information related thereto are disclosed in great detail above). Second, the collar device includes one or more sensors for monitoring/tracking/detecting physiological and motion metrics associated with a subject wearing the collar. Third, the collar device detects and receives data from environmental sensors that are (i) distributed throughout the premises and/or (ii) located within a beacon. The collar device may collect and process avoidance/interaction data, collar device sensor data (including physiological and motion activity data of a subject wearing the collar), and/or environmental sensor data to determine particular needs. As just one example and as further described below, the combination of avoidance/interaction data, physiological condition data, and/or environmental sensor data may indicate that an animal wearing the collar may be experiencing an audio disturbance, i.e. that the animal may benefit from sound masking.

As indicated above, a collar device may collect and process avoidance/interaction data, collar device sensor data (including physiological conditions and motion activity of a subject wearing the collar), and environmental sensor data to determine particular needs. It should be noted that a collar device may determine a need using any single type of data, i.e. avoidance/interaction, collar device sensor, and environmental, or using any combination of data types. Accordingly, data collection and analysis may be conducted by a collar device. However, data collection and analysis may also take place at a cloud computing level or on a smartphone device as described below.

As described above with respect to FIG. 12, a pet collar device, beacons, smartphone, environmental sensor and activity devices may be communicatively coupled via WPAN compatible communications (e.g. Bluetooth communications protocols under an embodiment) to a local router or communications hub providing a communicative coupling with wide area networks, metropolitan area networks and with the broader internet in general. Each such networked device within the monitoring/tracking/detection system may therefore be communicatively coupled to a remote cloud computing platform comprising one or more applications running on at least one processor of a remote server. Accordingly, the collar/beacons/smartphone, environmental sensors, and/or activity devices may transmit data to and/or receive data from a cloud computing platform. Under this embodiment, a collar device may collect and forward avoidance/interaction data, collar device sensor data (including physiological conditions and/or motion activity of a subject wearing the collar), and/or environmental sensor data. In other words, a collar device may collect and forward such data to a remote application running on a remote computing platform which may then itself analyze the data to determine a particular need of a subject wearing the collar device, i.e. that the animal may benefit from sound masking.

As described above, the collar/beacons/smartphone, environmental sensors, and/or activity devices may transmit data to and/or receive data from a cloud computing platform. Under this embodiment, a collar device may collect and forward avoidance/interaction data, collar device sensor data (including physiological conditions and/or motion activity of a subject wearing the collar), and/or environmental sensor data. In other words, a collar device may collect and forward such data to a remote application running on a remote computing platform. The remote application may then transmit this data to an application running on a smartphone or other mobile computing platform. The smartphone application may then analyze the data to determine a particular need of a subject wearing the collar device. Under an alternative embodiment, the smartphone device or other mobile computing platform may receive such data directly from the collar device and/or beacons through the network shown in FIG. 12 (and described in corresponding disclosure material).

Any combination of collar sensor data (including audio sensor data and/or piezo transducer data) and environmental data (including audio sensor data and/or piezo transducer data) may be used to determine the occurrence and characteristics of auditory events in the environment of a monitored animal. Further, any combination of collar sensor data (including audio sensor data and/or piezo transducer data) and environmental data (including audio sensor data and/or piezo transducer data) may be used to determine one or more behaviors indicating that an animal is experiencing an auditory disturbance. Note that information of the auditory event and/or animal behavior may be used (by a collar device, smartphone device, or remote computing platform) to automatically select one or more sound masking signals for delivery through a sound masking device and corresponding time intervals for delivery of such sound masking signals.

Any computing resource described above including collar device computing resources, smartphone application, and remote computing resources may be used to monitor the success of any delivered sound masking signal. The monitoring of each delivered sound masking signal includes monitoring the unwanted pet response before, during, and after delivery of the signal and logging any observed cessation, diminishment, or continuation of the unwanted pet response. Logged success data (i.e., cessation or diminishment data) may be used to determine future selections of sound masking signals.

Note that the sound masking collar device may provide a user with a direct interface for programming the device, i.e. selecting the time, duration, and type of sound masking signal.

Note that a user may predetermine whether a disturbing auditory condition exists based on the detection of certain auditory events. As just one example, a user of a monitoring/tracking/detection system (directed to a sound masking embodiment) may use a smartphone application or one or more applications communicatively coupled to the cloud computing environment (described above) to designate traffic noise (i.e. the sound of car horns) as a trigger for sound masking. When the systems and methods described above determine the occurrence of such traffic noise (i.e. the sound of car horns), the sound masking component emits a specified sound masking signal. Alternatively, a user may simple instruct the sound emitting component to emit selected sound masking signals at predetermined times or simply upon command.

A system is herein described that comprises a collar device including a sound masking component, the collar device including one or more collar device sensors for detecting physiological data of an animal. The system includes one or more environmental sensors for detecting environmental data of the animal's environment, the one or more environmental sensors including a transmitter for transmitting the environmental data. The system includes the collar device comprising a transceiver for receiving the environmental data. The system includes the collar device comprising one or more applications running on at least one processor for detecting an occurrence of one or more events using at least one of the physiological data, the environmental data, and outcome data. The system includes the one or more applications configured to use information of the one or more events to select a sound masking signal for delivery after the occurrence of the one or more events, wherein the sound masking signal comprises at least one selected combination of frequencies and amplitudes. The system includes the sound masking component for delivering the sound masking signal.

The at least one selected combination of an embodiment comprises white noise.

The at least one selected combination of an embodiment comprises pink noise.

The at least one selected combination of an embodiment comprises blue noise.

The at least one selected combination of an embodiment comprises violet noise.

The at least one selected combination of an embodiment comprises grey noise.

The one or more events comprise under an embodiment one or more of at least one auditory event in an environment of the animal and at least one behavior of the animal.

The at least one behavior of an embodiment indicates anxiety.

The at least one behavior of an embodiment comprises barking.

The at least one behavior of an embodiment comprises whining.

The at least one behavior of an embodiment comprises continued and rapid movement of the animal.

The at least one auditory event of an embodiment comprises one or more sounds in an environment of the animal including weather event noise, traffic noise, firework noise, and the audible presence of other animals The outcome data of an embodiment comprises a duration of the delivered sound masking signal.

The outcome data of an embodiment comprises a difference in a behavior of the animal at least one of before, during, and after the delivered sound masking signal.

The difference of an embodiment comprises a cessation of the at least one behavior.

The difference of an embodiment comprises a diminished occurrence of the at least one behavior.

The outcome data of an embodiment comprises continued occurrence of the at least one behavior.

The selecting the sound masking signal includes selecting time intervals for delivery of the sound masking signal, under an embodiment.

The one or more collar device sensors of an embodiment include a heart rate sensor for monitoring heart rate.

The one or more collar device sensors of an embodiment include an Electrocardiogram to monitor a heart's electrical activity (EKG or ECG).

The one or more collar device sensors of an embodiment include one or more blood pressure sensors to monitor blood pressure levels.

The one or more collar device sensors of an embodiment include one or more respiration rate sensors for monitoring respiration rates.

The one or more collar device sensors of an embodiment include one or more temperature sensors for monitoring body temperature.

The one or more collar device sensors of an embodiment include an accelerometer and/or gyroscope in order to monitor activity levels and activity types.

The one or more collar device sensors of an embodiment include one or more first acoustic sensors for detecting frequency, amplitude, and origin of audio signals.

The one or more collar device sensors of an embodiment include one or more first piezoelectric transducers for measuring ambient changes in one or more of pressure, temperature, and force.

The one or more first piezoelectric transducers of an embodiment include at least one piezoelectric transducer located on the animal for detecting auditory signals generated by the animal.

The one or more environmental sensors of an embodiment include temperature sensors.

The one or more environmental sensors of an embodiment include moisture sensors.

The one or more environmental sensors of an embodiment include humidity sensors.

The one or more environmental sensors of an embodiment include air pressure sensors and/or air quality condition sensors.

The one or more environmental sensors of an embodiment include a lightning detector sensor.

The one or more environmental sensors of an embodiment include one or more second acoustic sensors for detecting frequency, amplitude, and origin of audio signals.

The one or more environmental sensors of an embodiment include one or more second piezoelectric transducers for measuring ambient changes in one or more of pressure, temperature, and force.

A system is described herein that comprises a collar device including a sound masking component, the collar device including one or more collar device sensors for detecting physiological data of an animal. The system includes one or more environmental sensors for detecting environmental data of the animal's environment, the one or more environmental sensors including a transmitter for transmitting the environmental data. The system includes the collar device comprising a transceiver for receiving the environmental data. The system includes the collar device comprising one or more applications running on at least one processor for detecting an occurrence of one or more events using at least one of the physiological data, the environmental data, and outcome data. The system includes the one or more applications configured to use information of the one or more events to select a first sound masking signal for delivery after the occurrence of the one or more events, wherein the first sound masking signal comprises at least one first selected combination of frequencies and amplitudes, the one or more applications configured to provide information of the least one first selected combination to at least one remote computing device. The system includes receiving an instruction from the at least one remote computing device to deliver at least one of the first sound masking signal and a second sound masking signal, wherein the second sound masking signal comprises at least one second selected combination of frequencies and amplitudes. The system includes the sound masking component for delivering at least one of the first sound masking signal and the second sound masking signal.

Computer networks suitable for use with the embodiments described herein include local area networks (LAN), wide area networks (WAN), Internet, or other connection services and network variations such as the world wide web, the public internet, a private internet, a private computer network, a public network, a mobile network, a cellular network, a value-added network, and the like. Computing devices coupled or connected to the network may be any microprocessor controlled device that permits access to the network, including terminal devices, such as personal computers, workstations, servers, mini computers, main-frame computers, laptop computers, mobile computers, palm top computers, hand held computers, mobile phones, TV set-top boxes, or combinations thereof. The computer network may include one of more LANs, WANs, Internets, and computers. The computers may serve as servers, clients, or a combination thereof.

The systems and methods for providing a sound masking environment can be a component of a single system, multiple systems, and/or geographically separate systems. The systems and methods for providing a sound masking environment can also be a subcomponent or subsystem of a single system, multiple systems, and/or geographically separate systems. The components of the systems and methods for providing a sound masking environment can be coupled to one or more other components (not shown) of a host system or a system coupled to the host system.

One or more components of the systems and methods for providing a sound masking environment and/or a corresponding interface, system or application to which systems and methods for providing a sound masking environment are coupled or connected includes and/or runs under and/or in association with a processing system. The processing system includes any collection of processor-based devices or computing devices operating together, or components of processing systems or devices, as is known in the art. For example, the processing system can include one or more of a portable computer, portable communication device operating in a communication network, and/or a network server. The portable computer can be any of a number and/or combination of devices selected from among personal computers, personal digital assistants, portable computing devices, and portable communication devices, but is not so limited. The processing system can include components within a larger computer system.

The processing system of an embodiment includes at least one processor and at least one memory device or subsystem. The processing system can also include or be coupled to at least one database. The term "processor" as generally used herein refers to any logic processing unit, such as one or more central processing units (CPUs), digital signal processors (DSPs), application-specific integrated circuits (ASIC), etc. The processor and memory can be monolithically integrated onto a single chip, distributed among a number of chips or components, and/or provided by some combination of algorithms. The methods described herein can be implemented in one or more of software algorithm(s), programs, firmware, hardware, components, circuitry, in any combination.

The components of any system that include the systems and methods for providing a sound masking environment can be located together or in separate locations. Communication paths couple the components and include any medium for communicating or transferring files among the components. The communication paths include wireless connections, wired connections, and hybrid wireless/wired connections. The communication paths also include couplings or connections to networks including local area networks (LANs), metropolitan area networks (MANs), wide area networks (WANs), proprietary networks, interoffice or back-end networks, and the Internet. Furthermore, the communication paths include removable fixed mediums like floppy disks, hard disk drives, and CD-ROM disks, as well as flash RAM, Universal Serial Bus (USB) connections, RS-232 connections, telephone lines, buses, and electronic mail messages.

Aspects of the systems and methods for providing a sound masking environment and corresponding systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the systems and methods for providing a sound masking environment and corresponding systems and methods include: microcontrollers with memory (such as electronically erasable programmable read only memory (EEPROM)), embedded microprocessors, firmware, software, etc. Furthermore, aspects of the systems and methods for providing a sound masking environment and corresponding systems and methods may be embodied in microprocessors having software-based circuit emulation, discrete logic (sequential and combinatorial), custom devices, fuzzy (neural) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that any system, method, and/or other components disclosed herein may be described using computer aided design tools and expressed (or represented), as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, e-mail, etc.) over the Internet and/or other computer networks via one or more data transfer protocols (e.g., HTTP, FTP, SMTP, etc.). When received within a computer system via one or more computer-readable media, such data and/or instruction-based expressions of the above described components may be processed by a processing entity (e.g., one or more processors) within the computer system in conjunction with execution of one or more other computer programs.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import, when used in this application, refer to this application as a whole and not to any particular portions of this application. When the word "or" is used in reference to a list of two or more items, that word covers all of the following interpretations of the word: any of the items in the list, all of the items in the list and any combination of the items in the list.

The above description of embodiments of the systems and methods for providing a sound masking environment and corresponding systems and methods is not intended to be exhaustive or to limit the systems and methods to the precise forms disclosed. While specific embodiments of, and examples for, the systems and methods for providing a sound masking environment and corresponding systems and methods are described herein for illustrative purposes, various equivalent modifications are possible within the scope of the systems and methods, as those skilled in the relevant art will recognize. The teachings of the systems and methods for providing a sound masking environment and corresponding systems and methods provided herein can be applied to other systems and methods, not only for the systems and methods described above.

The elements and acts of the various embodiments described above can be combined to provide further embodiments. These and other changes can be made to the systems and methods for providing a sound masking environment and corresponding systems and methods in light of the above detailed description.

We claim:

1. A system comprising,
a collar device including a sound masking component, the collar device including one or more collar device sensors for detecting physiological data of an animal;
the collar device including one or more environmental sensors for detecting environmental data of the animal's environment;
the collar device comprising one or more applications running on at least one processor for detecting an occurrence of one or more events using at least one of the physiological data and the environmental data, wherein the one or more events comprise one or more of at least one auditory event in an environment of the animal and at least one behavior of the animal;
the one or more applications for using outcome data and information of the one or more events to select a sound masking signal for delivery after the occurrence of the one or more events, wherein the outcome date comprises a previously detected difference in a behavior of the animal in response to at least one sound masking signal previously delivered by the sound masking component, wherein the sound masking signal comprises at least one selected combination of frequencies and amplitudes;
the sound masking component for delivering the sound masking signal; and
the one or more applications for logging the outcome date over time, the logging the outcome date including updating the outcome data to include a difference in the at least one behavior of the animal in response to the delivered sound masking signal, wherein the difference in the at least one behavior of the animal is determined using the physiological data of the animal and the environmental data of the animal's environment.

2. The system of claim 1, wherein the at least one selected combination comprises white noise.

3. The system of claim 1, wherein the at least one selected combination comprises pink noise.

4. The system of claim 1, wherein the at least one selected combination comprises blue noise.

5. The system of claim 1, wherein the at least one selected combination comprises violet noise.

6. The system of claim 1, wherein the at least one selected combination comprises grey noise.

7. The system of claim 1, wherein the at least one behavior indicates anxiety of the animal.

8. The system of claim 1, wherein the at least one behavior comprises barking of the animal.

9. The system of claim 1, wherein the at least one behavior comprises whining of the animal.

10. The system of claim 1, wherein the at least one behavior comprises continued and rapid movement of the animal.

11. The system of claim 1, wherein the at least one auditory event comprises one or more sounds in the environment of the animal including weather event noise, traffic noise, firework noise, and an audible presence of other animals.

12. The system of claim 1, wherein the difference in the at least one behavior of the animal comprises a cessation of the at least one behavior.

13. The system of claim 1, wherein the difference in the at least one behavior of the animal comprises a diminished occurrence of the at least one behavior.

14. The system of claim 1, the selecting the sound masking signal including selecting time intervals for delivery of the sound masking signal.

15. The system of claim 1, wherein the one or more collar device sensors include a heart rate sensor for monitoring heart rate of the animal.

16. The system of claim 1, wherein the one or more collar device sensors include an Electrocardiogram to monitor a heart's electrical activity (EKG or ECG) of the animal.

17. The system of claim 1, wherein the one or more collar device sensors include one or more blood pressure sensors to monitor blood pressure levels of the animal.

18. The system of claim 1, wherein the one or more collar device sensors include one or more respiration rate sensors for monitoring respiration rates of the animal.

19. The system of claim 1, wherein the one or more collar device sensors include one or more temperature sensors for monitoring body temperature of the animal.

20. The system of claim 1, wherein the one or more collar device sensors include an accelerometer and/or gyroscope in order to monitor activity levels and activity types of the animal.

21. The system of claim 1, wherein the one or more collar device sensors include one or more first acoustic sensors for detecting frequency, amplitude, and origin of audio signals, wherein the audio signals include the at least one auditory event.

22. The system of claim 1, wherein the one or more collar device sensors include one or more first piezoelectric transducers for measuring ambient changes in one or more of pressure, temperature, and force.

23. The system of claim 22, wherein the one or more first piezoelectric transducers include at least one piezoelectric transducer located on the animal for detecting auditory signals generated by the animal.

24. The system of claim 1, wherein the one or more environmental sensors include temperature sensors.

25. The system of claim 1, wherein the one or more environmental sensors include moisture sensors.

26. The system of claim 1, wherein the one or more environmental sensors include humidity sensors.

27. The system of claim 1, wherein the one or more environmental sensors include air pressure sensors and/or air quality condition sensors.

28. The system of claim 1, wherein the one or more environmental sensors include a lightning detector sensor.

29. The system of claim 1, wherein the one or more environmental sensors include one or more second acoustic sensors for detecting frequency, amplitude, and origin of audio signals, wherein the audio signals include the at least one auditory event.

30. The system of claim 1, wherein the one or more environmental sensors include one or more second piezoelectric transducers for measuring ambient changes in one or more of pressure, temperature, and force.

31. A system comprising,
a collar device including a sound masking component, the collar device including one or more collar device sensors for detecting physiological data of an animal;
one or more environmental sensors for detecting environmental data of the animal's environment, the one or more environmental sensors including a transmitter for transmitting the environmental data;
the collar device comprising a transceiver for receiving the environmental data;
the collar device comprising one or more applications running on at least one processor for detecting an occurrence of one or more events using at least one of the physiological data and the environmental data, wherein the one or more events comprise one or more of at least one auditory event in an environment of the animal and at least one behavior of the animal;
the one or more applications for using outcome data and information of the one or more events to select a first sound masking signal for delivery after the occurrence of the one or more events, wherein the outcome date comprises a previously detected difference in a behavior of the animal in response to at least one sound masking signal previously delivered by the sound masking component, wherein the first sound masking signal comprises at least one first selected combination of frequencies and amplitudes, the one or more applications for providing information of the least one first selected combination to at least one remote computing device;
the one or more applications for receiving an instruction from the at least one remote computing device to deliver at least one of the first sound masking signal and a second sound masking signal, wherein the second sound masking signal comprises at least one second selected combination of frequencies and amplitudes;
the sound masking component for delivering at least one of the first sound masking signal and the second sound masking signal; and
the one or more applications for logging the outcome date over time, the logging the outcome date including updating the outcome data to include a difference in the at least one behavior of the animal in response to delivery of the at least one of the first sound masking signal and the second sound masking signal, wherein the difference in the at least one behavior of the animal is determined using the physiological data of the animal and the environmental data of the animal's environment.

32. A system comprising,
a collar device including a sound masking component, the collar device including one or more collar device sensors for detecting physiological data of an animal;
one or more environmental sensors for detecting environmental data of the animal's environment, the one or more environmental sensors including a transmitter for transmitting the environmental data;
the collar device comprising a transceiver for receiving the environmental data;
the collar device comprising one or more applications running on at least one processor for detecting an occurrence of one or more events using at least one of the physiological data and the environmental data, wherein the one or more events comprise one or more of at least one auditory event in an environment of the animal and at least one behavior of the animal;
the one or more applications for using outcome data and information of the one or more events to select a sound masking signal for delivery after the occurrence of the one or more events, wherein the outcome data comprises a previously detected difference in a behavior of the animal in response to at least one sound masking signal previously delivered by the sound masking component, wherein the sound masking signal comprises at least one selected combination of frequencies and amplitudes;

the sound masking component for delivering the sound masking signal; and the one or more applications for logging the outcome data over time, the logging the outcome data including updating the outcome data to include a difference in the at least one behavior of the animal in response to the delivered sound masking signal, wherein the difference in the at least one behavior of the animal is determined using the physiological data of the animal and the environmental data of the animal's environment.

* * * * *